United States Patent
Bozich et al.

[11] Patent Number: 5,386,689
[45] Date of Patent: Feb. 7, 1995

[54] ACTIVE GAS TURBINE (JET) ENGINE NOISE SUPPRESSION

[75] Inventors: Daniel J. Bozich, San Diego, Calif.; Robert Wagenfeld, Westport, Conn.

[73] Assignee: Noises Off, Inc., White Plains, N.Y.

[21] Appl. No.: 961,612

[22] Filed: Oct. 13, 1992

[51] Int. Cl.$^6$ .................. F02G 1/00; A61F 11/06; H04R 3/02
[52] U.S. Cl. .................. 60/39.33; 415/119; 381/71; 381/73.1
[58] Field of Search ............ 60/39.33; 415/119; 381/71, 73.1

[56] References Cited

U.S. PATENT DOCUMENTS

| | | | |
|---|---|---|---|
| 3,936,606 | 2/1976 | Wanke . | |
| 4,044,203 | 8/1977 | Swinbanks | 179/1 P |
| 4,489,441 | 12/1984 | Chaplin | 381/71 |
| 4,689,821 | 8/1987 | Salikuddin et al. | 381/71 |
| 4,947,434 | 8/1990 | Ito | 381/71 |
| 4,987,598 | 1/1991 | Eriksson | 381/71 |
| 5,010,576 | 4/1991 | Hill | 381/71 |
| 5,018,202 | 5/1991 | Takahashi et al. | 381/71 |
| 5,022,082 | 6/1991 | Eriksson et al. | 381/71 |
| 5,131,047 | 7/1992 | Hashimoto et al. | 381/73.1 |
| 5,138,664 | 8/1992 | Kimura et al. | 381/71 |
| 5,195,140 | 3/1993 | Kudo et al. | 381/71 |

OTHER PUBLICATIONS

Widrow, B. & Stearns, S., "Adaptive Signal Processing" 1985 pp. 270-297.

*Primary Examiner*—Richard A. Bertsch
*Assistant Examiner*—Howard R. Richman
*Attorney, Agent, or Firm*—Gottlieb, Rackman & Reisman

[57] ABSTRACT

A method and a system for reducing the acoustic levels of internal and external sound fields generated by gas turbine engines has several actuators to generate sound, several sensors to measure the acoustic levels, and one or more controllers, The controllers are adaptive self-learning neural networks that control the actuators to generate sound in order to effect the reduction of the internal and external sound field as measured by the Sensors.

14 Claims, 28 Drawing Sheets

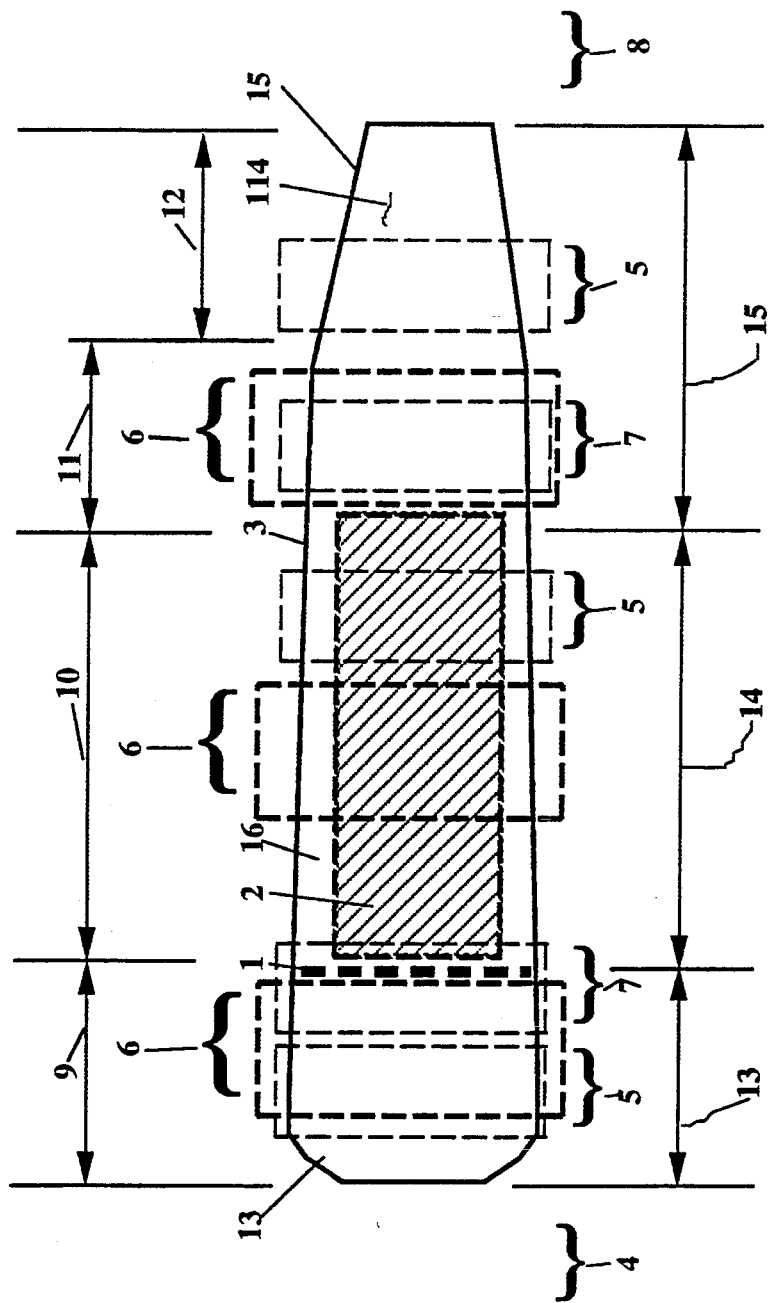

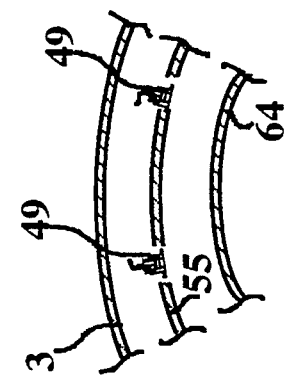
FIGURE 2F
FIGURE 2I
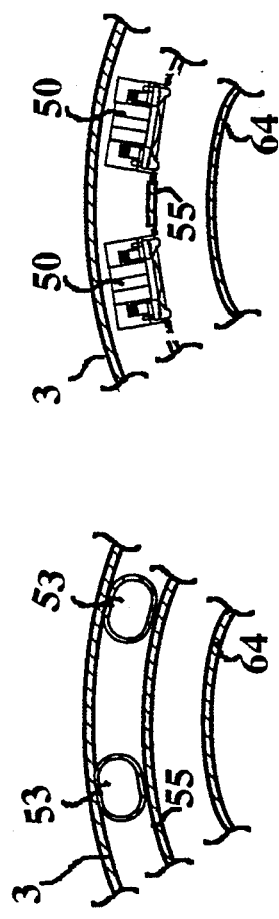
FIGURE 2G
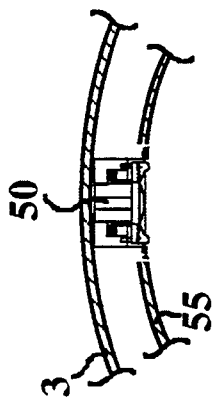
FIGURE 2H
FIGURE 2D
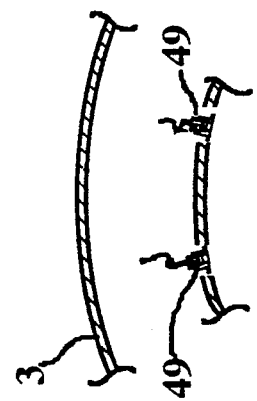
FIGURE 2B

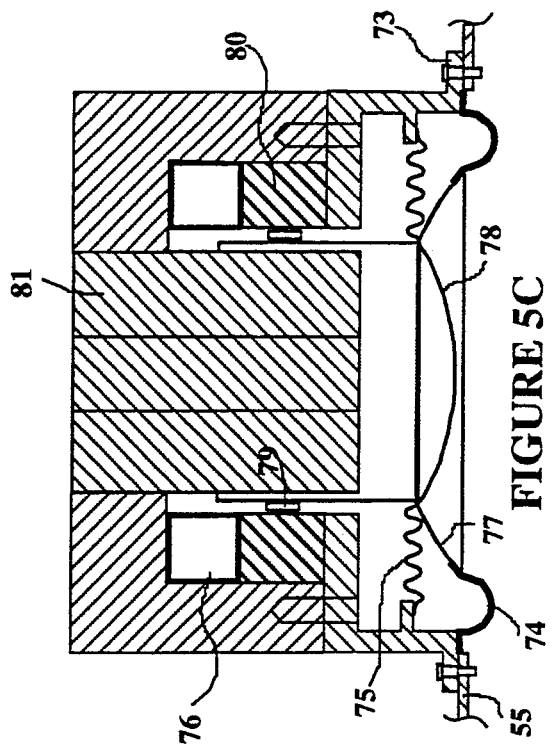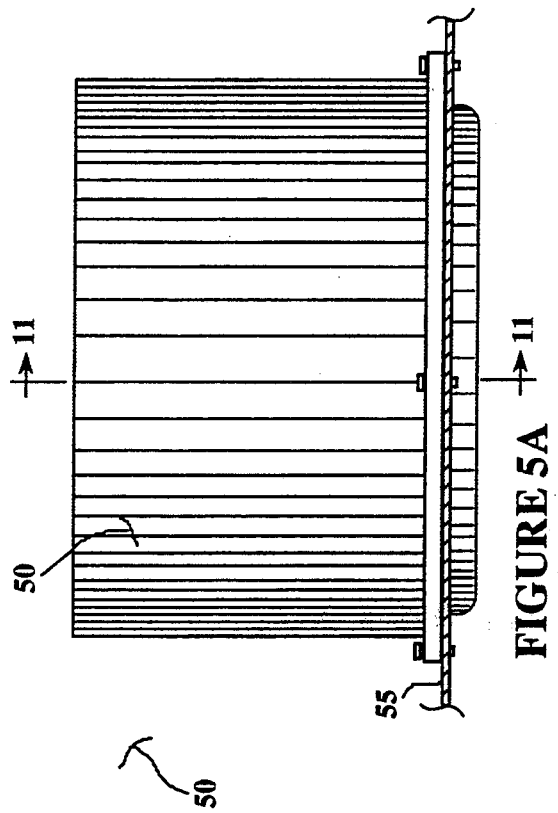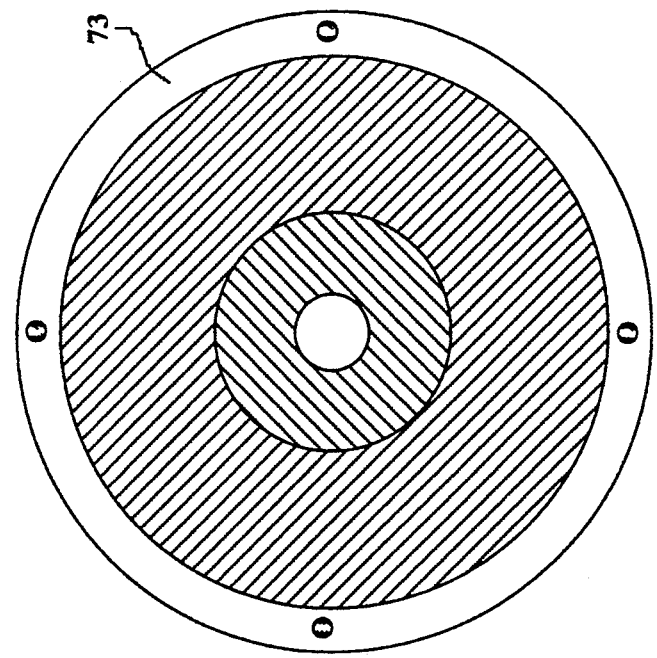

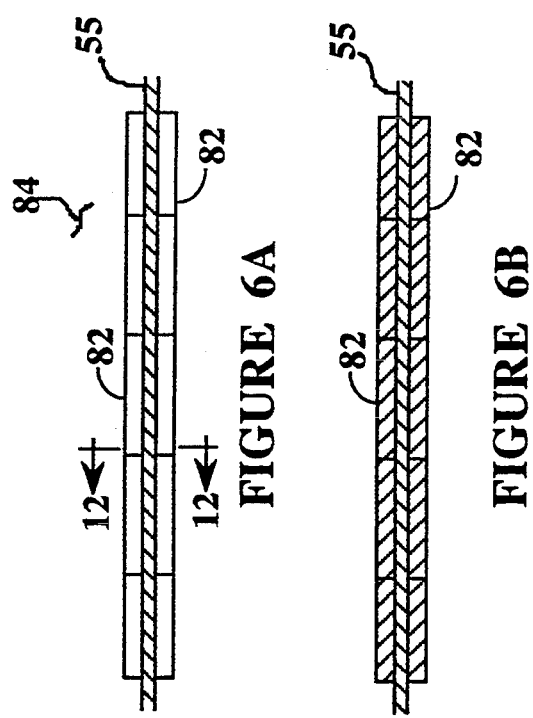

SAMPLED WAVEFORM
SPECTRUM
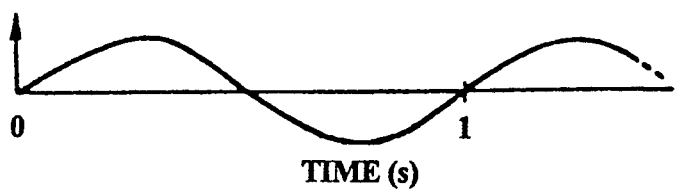
A. $f_{k\phi} = 1$ Hz; $f_c = 4$ Hz
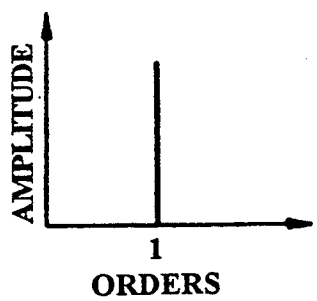
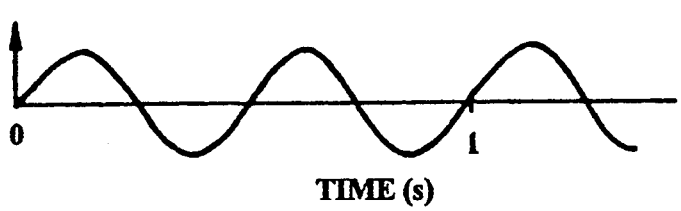
B. $f_{k\phi} = 2$ Hz; $f_c = 8$ Hz
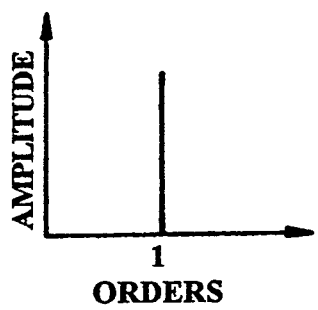
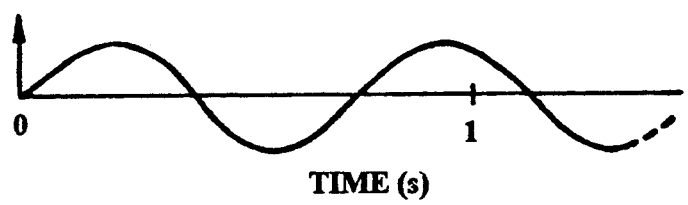
C. $f_{k\phi} = 1.5$ Hz; $f_c = 6$ Hz
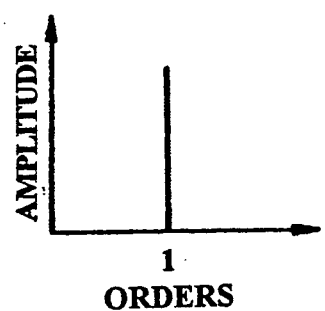
FIGURE 9A

ACTIVE GAS TURBINE (JET) ENGINE NOISE SUPPRESSION

This invention relates to acoustical apparatus, and to methods to actively and adaptively suppress acoustic noise, such as an adaptive vibration control system. In particular it relates to such apparatus and methods for suppressing acoustic noise produced internally and externally by a jet (gas turbine) engine and perceived far from the engine.

BACKGROUND OF THE INVENTION

Commercial jet aircraft currently are required to meet governmentally specified perceived noise criteria. The prior systems used in engine silencing include both passive and active methods and apparatus. Passive means include mufflers, acoustic treatment in the inlets and exhaust ducts and tailpipes. Active means include engine surge control, turbofans with high bypass ratios, bypass/exhaust mixers, external suppressors, and acoustic wave interference in engine inlet ducts, exhaust tailpipes, and mufflers.

The previous art, for example, Wanke U.S. Pat. No. 3,936,606, issued Feb. 3, 1976, utilized acoustic wave interference to achieve sound reduction in gas turbine engines. A microphone, or equivalent, measured the existing acoustic wave. Conventional adaptive control apparatus created a time-delayed and phase reversed mirror symmetry signal to generate an anti-noise acoustic wave downstream from the microphone via a "speaker" in a turbojet's inlet duct and exhaust tailpipe. The Wanke patent, however required detailed modelling of the acoustic wave and the counter wave that would cancel it. Since the wave that effected cancellation was a simple time delayed and phase reversed wave front, Wanke found it necessary to direct the waves through a wave guide that converted all the wave energy of both the acoustic wave and the counter wave into plane waves or other predictable wave modes. Cancellation could only be accomplished within such wave guides, and therefore they had to be present within the region where the acoustic energy would be canceled. The use of such conventional noise control systems has had limited results in turbojet engine inlet ducts.

Other prior systems of active noise suppression on gas turbines has not produced cancellation of non-linear, random noise over the needed acoustic frequency range in real time.

The prior methods and apparatus for active sound control, noise cancellation, noise abatement, noise attenuation, and the like, involve conventional adaptive controllers or adaptive filters. These systems require extensive system modeling in order to operate successfully. They have limited abilities in non-stationary and non-linear acoustic applications.

BRIEF DESCRIPTION OF THE INVENTION

The invention realizes a reliable, adaptable, and cost-effective means to upgrade aircraft jet engines to meet current and future noise criteria. The methods of this invention also has application to helicopter, industrial and military gas turbine engines. They also may be applicable to steam turbines, reciprocating engines, and electrical moron acoustic noise as well. The invention provides an active apparatus and method for significantly reducing the acoustic levels of sound generated by gas turbine and other engines. The reductions of the sound level on aircraft gas turbine (jet) engines are addressed specifically in this patent description; however, the invention is not limited to jet turbine engines.

In the present invention, sound sources that are installed at appropriate locations within the gas turbine engine are the noise suppression means. The system that controls these sound sources learns, self tunes, and adapts to the in situ noise environments to produce acoustic waves. The acoustic waves are equal to and opposite to the mixture of periodic, harmonic, and random noise acoustic waves produced by the gas turbine's internal processes. The two sets of acoustic waves are nearly mirror images of each other. Therefore, their mutual interference causes them to cancel each other. This process reduces the sound levels produced within the engine. Also, this process reduces the sound levels externally propagated from the engine. Measurements of any residual acoustic waves assess the effectiveness of the cancellation process. The residual acoustic signals become the error signals fed back to the control system. The control system learns to minimize the error signals under time-varying (non-stationary) conditions. Thus the final, residual acoustic noise field is minimized.

The primary advantage of this invention over the prior systems is its ability to tune itself in situ to variations measured downstream from both the engine's acoustic noise sources and the canceling acoustic noise generators.

The Structure Of Gas Turbine Engines

To appreciate the context in which the present invention was made, it is necessary to have some understanding of the structure of gas turbine engines. A gas turbine has two main acoustic energy paths to the atmosphere, namely, its air inlet and its exhaust outlet. Within the engine there are two major energy paths. The fan bypass duct represents one path. The air compressor/combustion and gas generator/gas turbine/exhaust duct is the other path. Air entering the inlet is compressed by the bypass fan stage and divided between the bypass duct and the low pressure compressor inlet duct. The air in the bypass duct continues through to the exhaust end of the engine. Successive compressor stages of the low pressure compressor compress the remaining air until it enters the high pressure compressor. The high pressure compressor further compresses this air in successive stages. High pressure air enters the combustion chambers, mixes with fuel and ignites to produce large amounts of high temperature, high pressure gas. This gas drives successive power turbine sections. The successive power turbine stages provide power to the compressor sections including the bypass fan. The flow of hot exhaust gas from the power turbines enters the exhaust tailpipe section where it mixes with the cooler bypass air. This total air/gas mass flow provides the engine thrust,

Sound Sources In Gas Turbine Engines

An operating gas turbine engine presents three significant acoustic noise sources to the surrounding air medium. The primary noise source is the engine exhaust. Another noise source is the air inlet. Mechanical engine noises that radiate through the nacelle structures represent a third acoustic source of an operating engine.

The Location Of Sound Suppression Sources

Therefore, a plurality of acoustic sources placed within the bypass air ducts and exhaust ducts suppress the rearward-radiated exhaust noise. Acoustic cancellation source locations are at or near the junction where the bypass air meets and mixes with the exhaust gas. An additional plurality of acoustic sources placed in the inlet duct suppress the forward-radiated inlet noise. If necessary, an additional plurality of vibration/acoustic sources placed on or near the engine structures suppress the mechanically radiated noise.

Neurocontroller Suppression

Microphones, or equivalents (such as dynamic pressure sensors, and/or accelerometers) strategically placed in and around the engines, on the aircraft fuselage, wings, nacelles, tail, and stabilizer structures measure the resulting residual sound levels. A neural network is used to control the acoustic sources that effect the noise cancellation. This network is termed a neurocontroller.

The measurements of residual sound levels provide 'error' signals to the neurocontroller for adaptive suppression of the engine noise. The neurocontroller will continue to minimize the sound levels at the measurement locations by controlling the plurality of acoustic sources at all locations. The neuro-controller produces sound waves that interfere destructively with the engine-produced sound waves. This wave interference process cancels these latter waves. The net result is suppression of the external acoustic field produced by the operating engines.

The system of the present invention comprises a plurality of means to generate sound (termed the 'Actuators'); a plurality of means to measure sound (termed the 'Sensors'); one or more adaptive, self-learning, neural network-based Controllers (termed the 'Controllers'.) The Controllers control the plurality of Actuators to affect the reduction of the measured internal and external sound field. This system is integrated, installed, and operated on one or more engines (termed the 'Apparatus').

The preferred embodiments of the present invention have the following features:

The acoustic sources comprise high-intensity Actuators that include high-intensity air-stream modulators, high-intensity speakers, and high-intensity mechanical actuators. These Actuators may be placed inside the engine to suppress the noise at or very near the noise sources, Air modulator-based acoustic sources may be employed that use a flow of compressed air. Adequate compressed air for these Actuators is available from appropriate compression stages of the operating turbofan engine to achieve a very energy-efficient operation.

The Sensors that control performance of the noise suppression system are located both inside the engine and in the far and near external radiation fields of the engine. A plurality of such error sensors control a plurality of Actuators simultaneously to suppress acoustic noise from multiple engines. That is, the controller is a Multiple-Input, Multiple-Output (MIMO) neuro-controller.

The neural network based controller is of a unique form. It has the following features: It incorporates a MIMO neurocontroller that includes one or more neural network based embodiments of the filtered-x algorithm. It includes one are more MIMO neuroemulators that automatically learn, in situ, the acoustic-coupled transfer functions between the pluralities of both error Sensors and Actuators. It includes one or more MIMO neurocontrollers that automatically learn, in situ, to control the plurality of Actuators simultaneously to suppress the sound at the plurality of error Sensor locations.

As a result, the system of the present invention learns and adapts in real time to changes in engine performance, aircraft operation, and external aircraft environment. It may be synchronized by engine keyphasors or tachometers. It learns and adapts in real time to changes in residual acoustic fields. It is non-obtrusive to engine performance without degrading fuel performance since the system is lightweight, efficient, and has low electrical-power use. The system is adaptable to both gas and steam turbines. The system is adaptable to other rotating engines and machinery types.

BRIEF DESCRIPTION OF THE DRAWINGS

The above description, as well as further objects, features and advantages of the present invention, will be mope fully appreciated by reference to the following detailed description of a presently preferred, but nonetheless illustrative, embodiment in accordance with the present invention when taken in conjunction with the accompanying drawings wherein:

FIG. 1A illustrates a side view of the major sections of a turbofan engine and the zones of the engine and nacelle reserved for the installations of Actuators and Sensors.

Figure 2A:
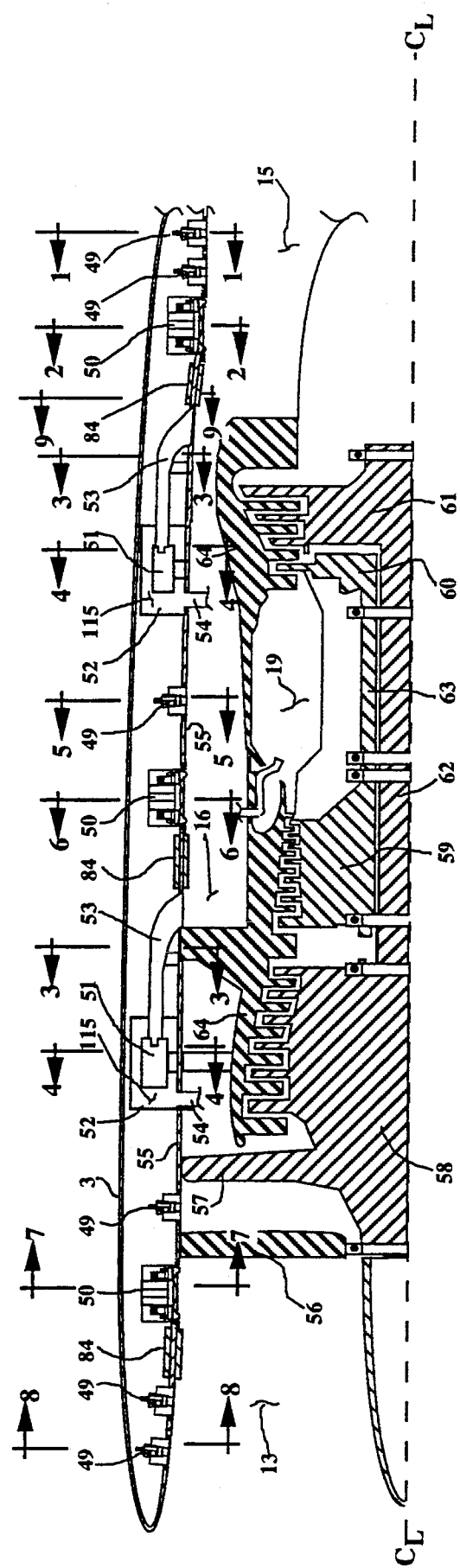
FIG. 2A is one embodiment of the Invention illustrating a side cross-section of part of a turbofan engine.

Fig, 2D is a cross-section along lines 2—2 of FIG. 2A.

FIG. 2D is a cross-section along lines 3—3 of FIG. 2A.

Figure 2J:
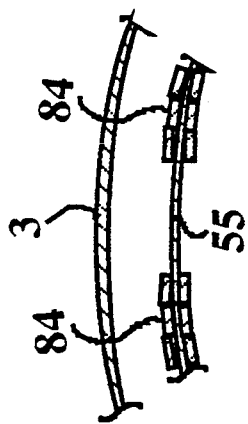
FIG. 2B is a cross-section along lines 1—1 of FIG. 2A.
Figure 2C:
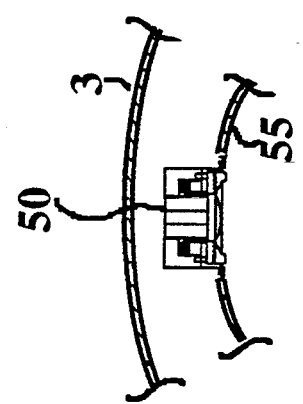
Figure 2E:
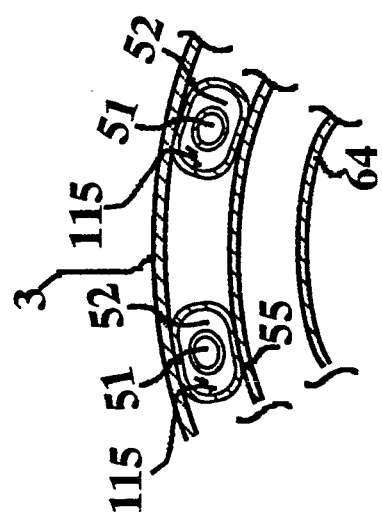

FIG. 2E is a cross-section along lines 4—4 of FIG. 2A.

FIG. 2F is a cross-section along lines 5—5 of FIG. 2A.

FIG. 2G is a cross-section along lines 6—6 of FIG. 2A.

FIG. 2H is a cross-section along lines 7—7 of FIG. 2A.

FIG. 2I is a cross-section along lines 8—8 of FIG. 2A.

FIG. 2J is a cross-section along lines 8—8 of FIG. 2A.

Figure 3:
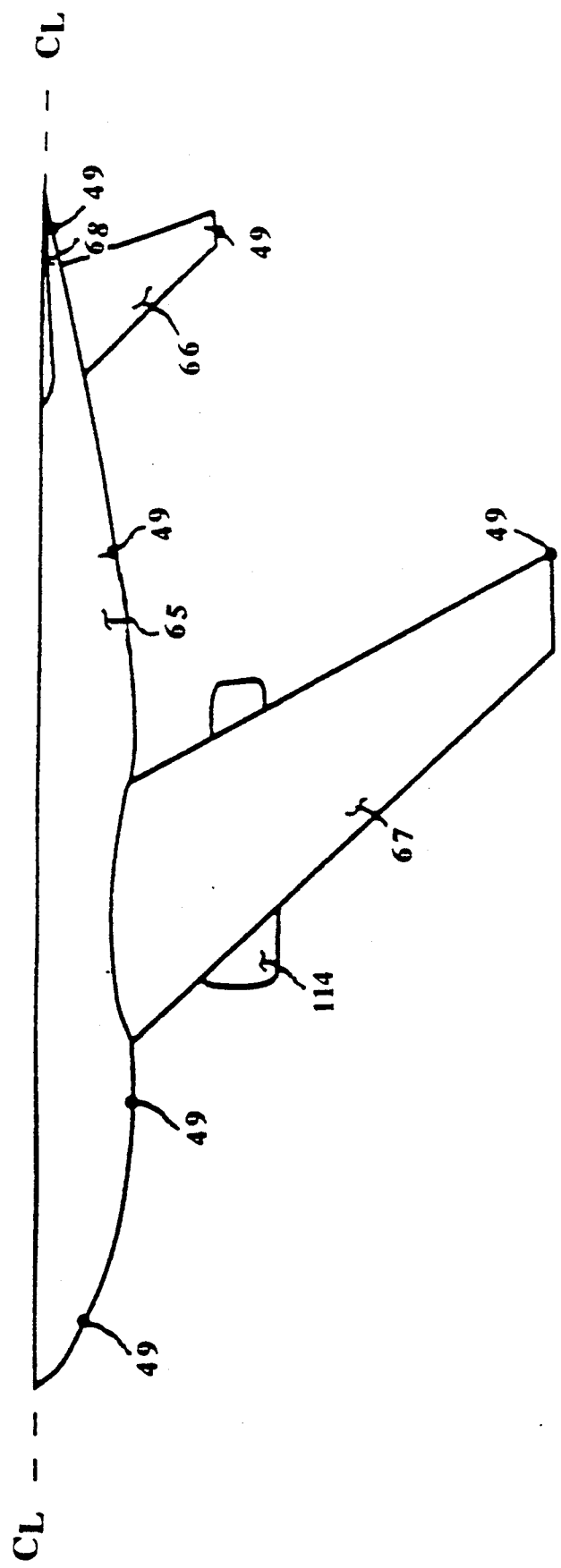

FIG. 3 is a plan view of a typical aircraft showing typical additional Sensor locations.

Figure 4A:
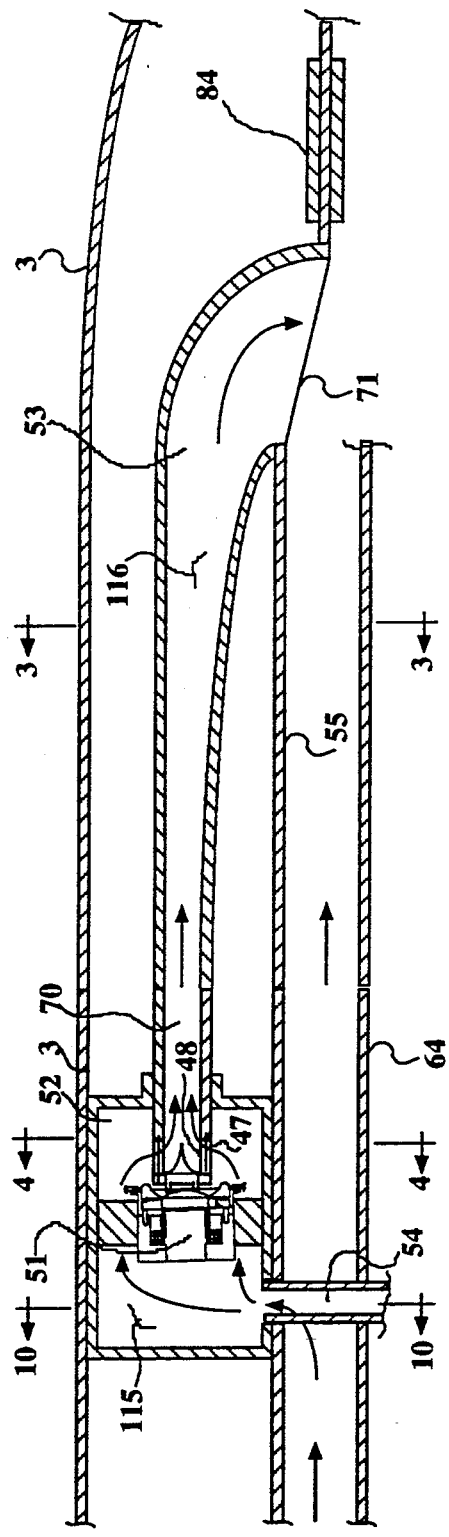

FIG. 4A is a cross-section view of a typical air modulator and horn.

Figure 4C:
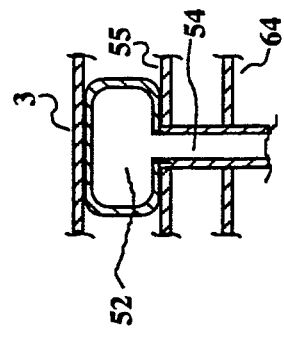
Figure 4B:
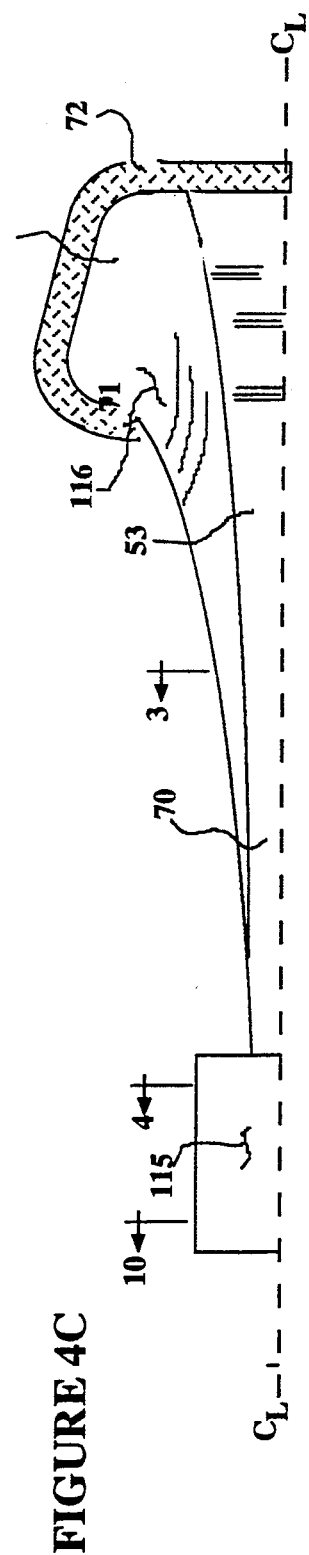

FIG. 4B is a plan view of a typical impedance-matching acoustic horn.

FIG. 4C is a cross-section along lines 10—10 of FIG. 4A,

FIG. 5A is a side plan view of a typical high-intensity speaker.

FIG. 5B is a top plan view of a typical high intensity speaker.

FIG. 5C is a cross-section along lines L—L of FIG. 5A.

FIG. 6A is a side plan view of a typical high-force piezoceramic Actuator 'patch'.

FIG. 6B is a cross-section along lines 12—12 of FIG. 6A.

Figure 7:
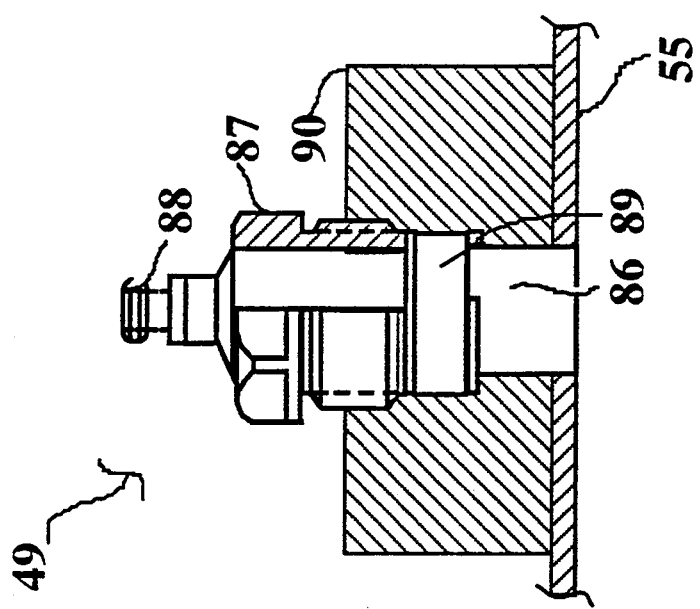

FIG. 7 is a plan view of a typical internal sensor installation along the lines 1—1, 5—5 and 8—8 of FIG. 2A.

Figure 8:
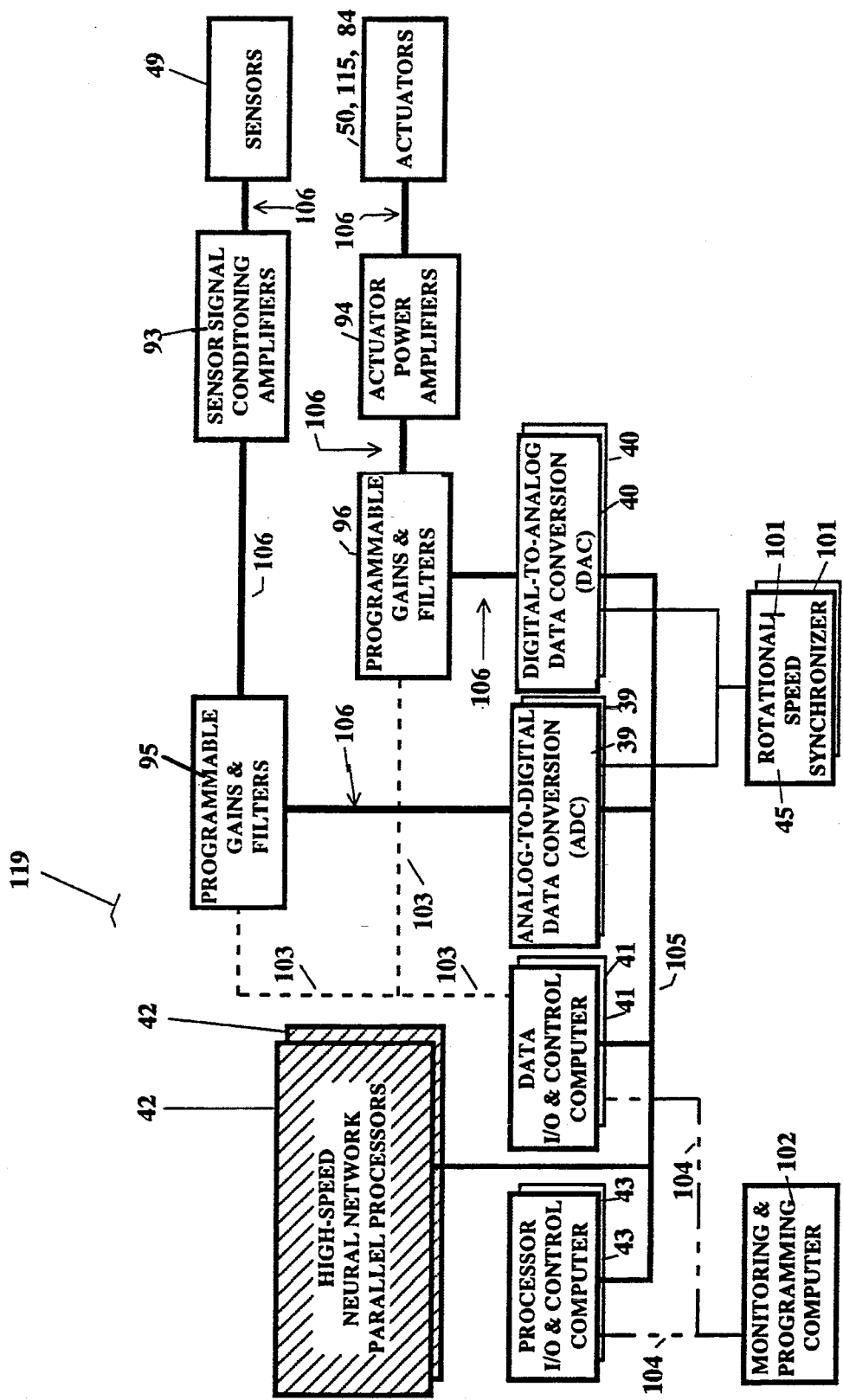

FIG. 8 is a schematic of typical instrumentation installed on a two-engine aircraft.

FIG. 9A, 9B, 90 and 9D are a schematic block diagrams illustrating the processes of Controller synchronization.

Figure 10A:
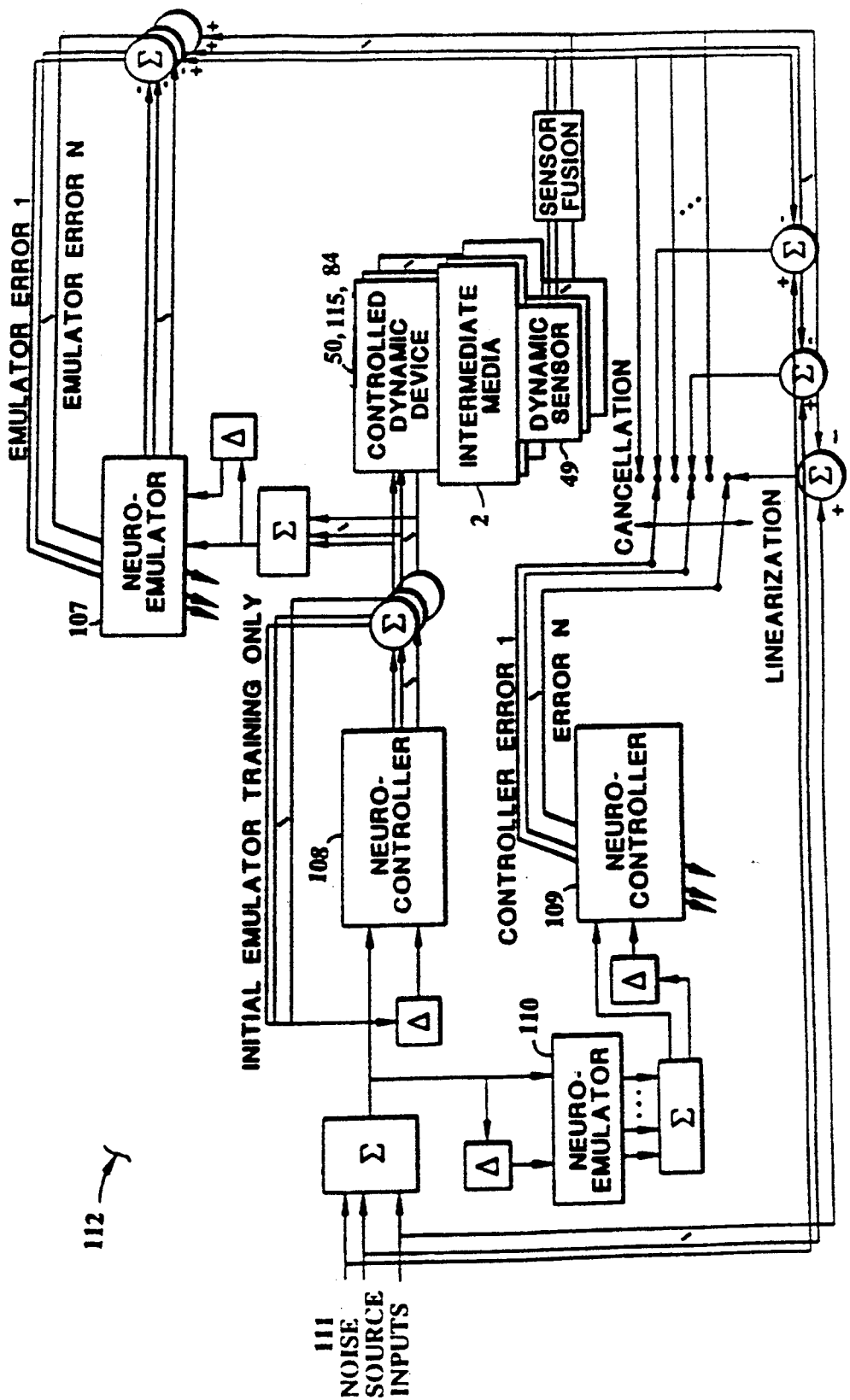

FIG. 10A is a block diagram of a typical embodiment of the neural network based filtered-x algorithm implemented in the current noise suppression MIMO neurocontroller.

Figure 10B:
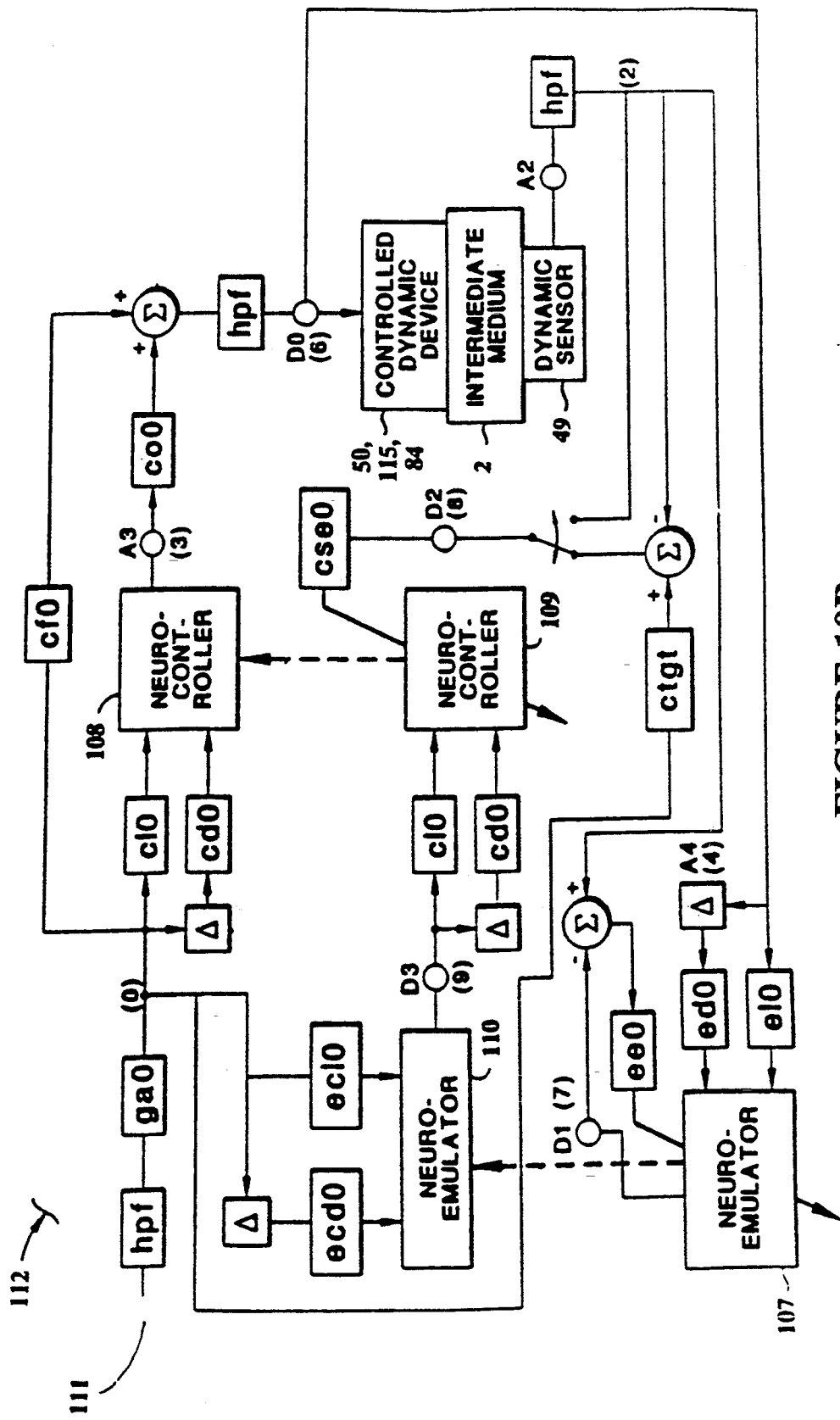

FIG. 10B illustrates a block diagram of a preferred single-input neurocontroller for use in the present invention when only one cancellation actuator is used.

Figure 1B:
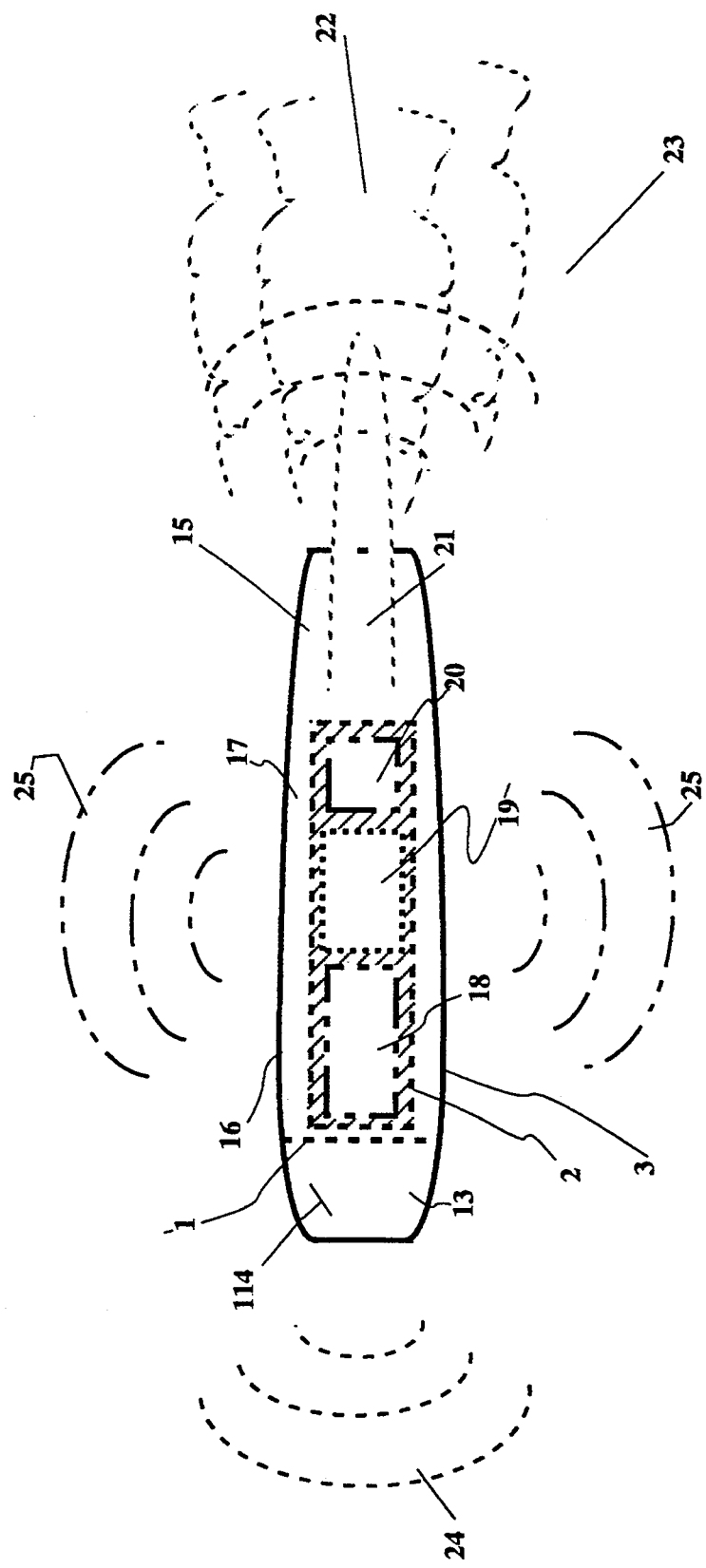
Fig. 1B is a schematic diagram showing the primary noise source locations relative to a turbofan engine.
Figure 1C:
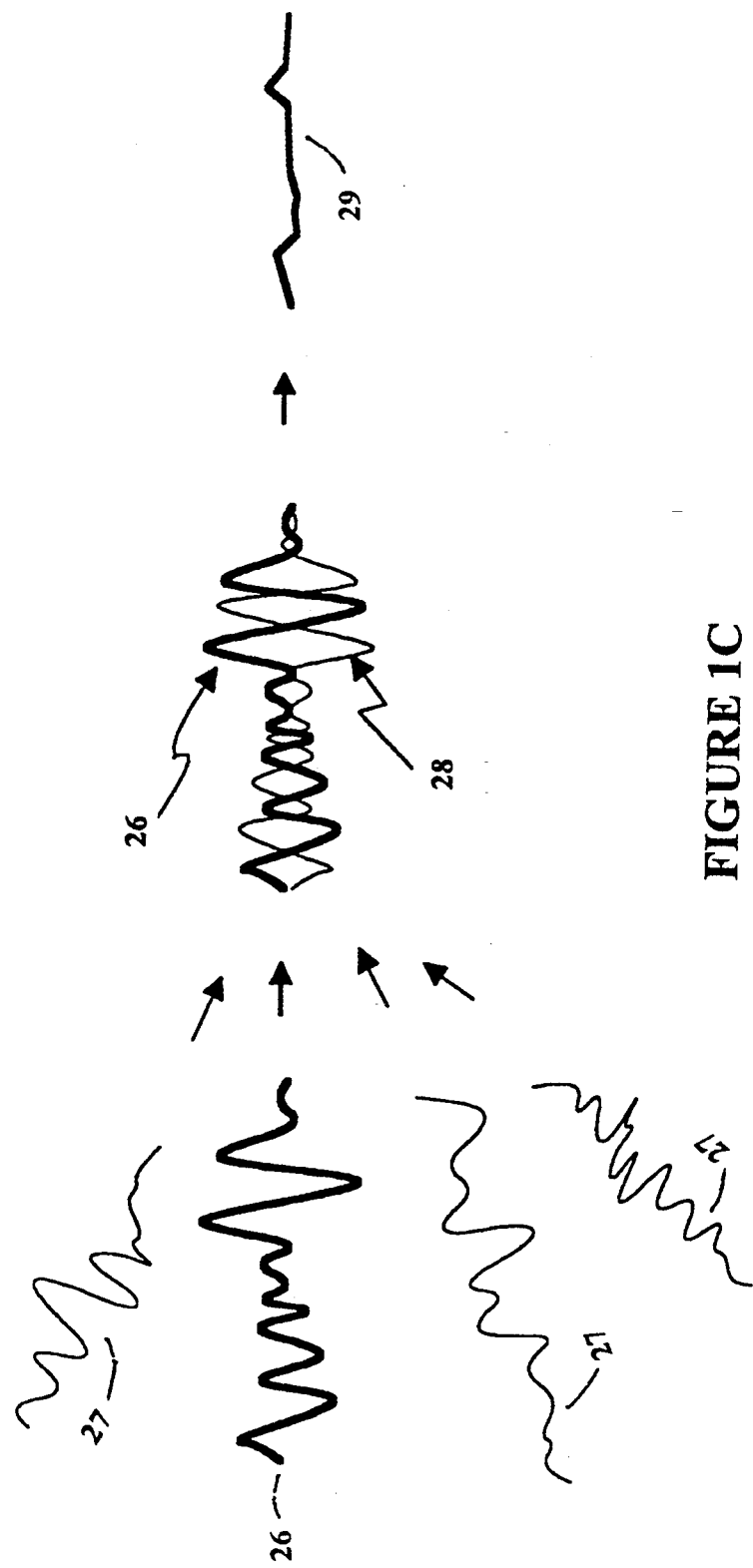
FIG. 1C illustrates the process of wave cancellation by wave interference.
Figure 1D:
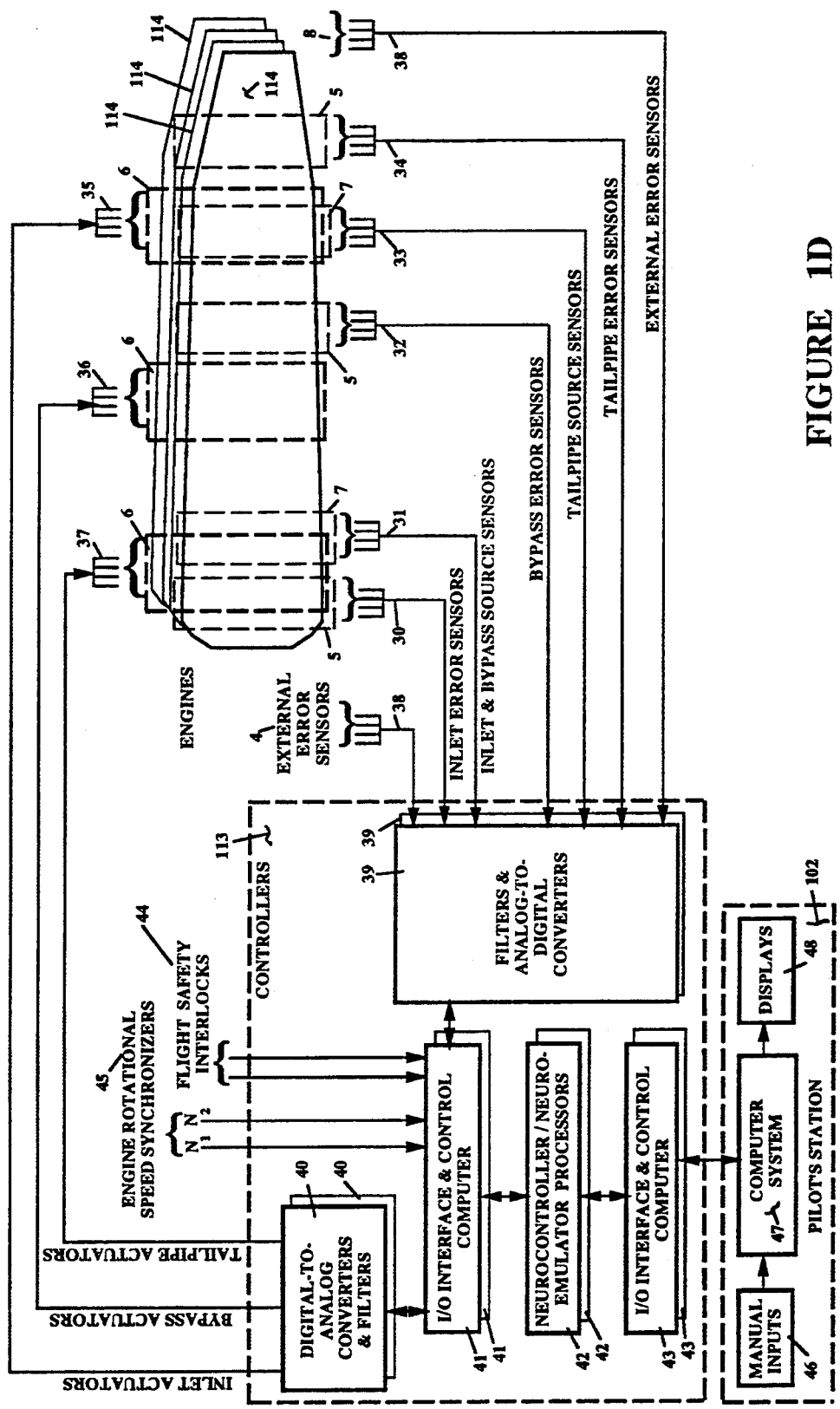
FIG. 1D is a partly block, partly schematic diagram of a novel method and Apparatus for suppressing acoustic noise by use of wave interference.
Figure 10C:
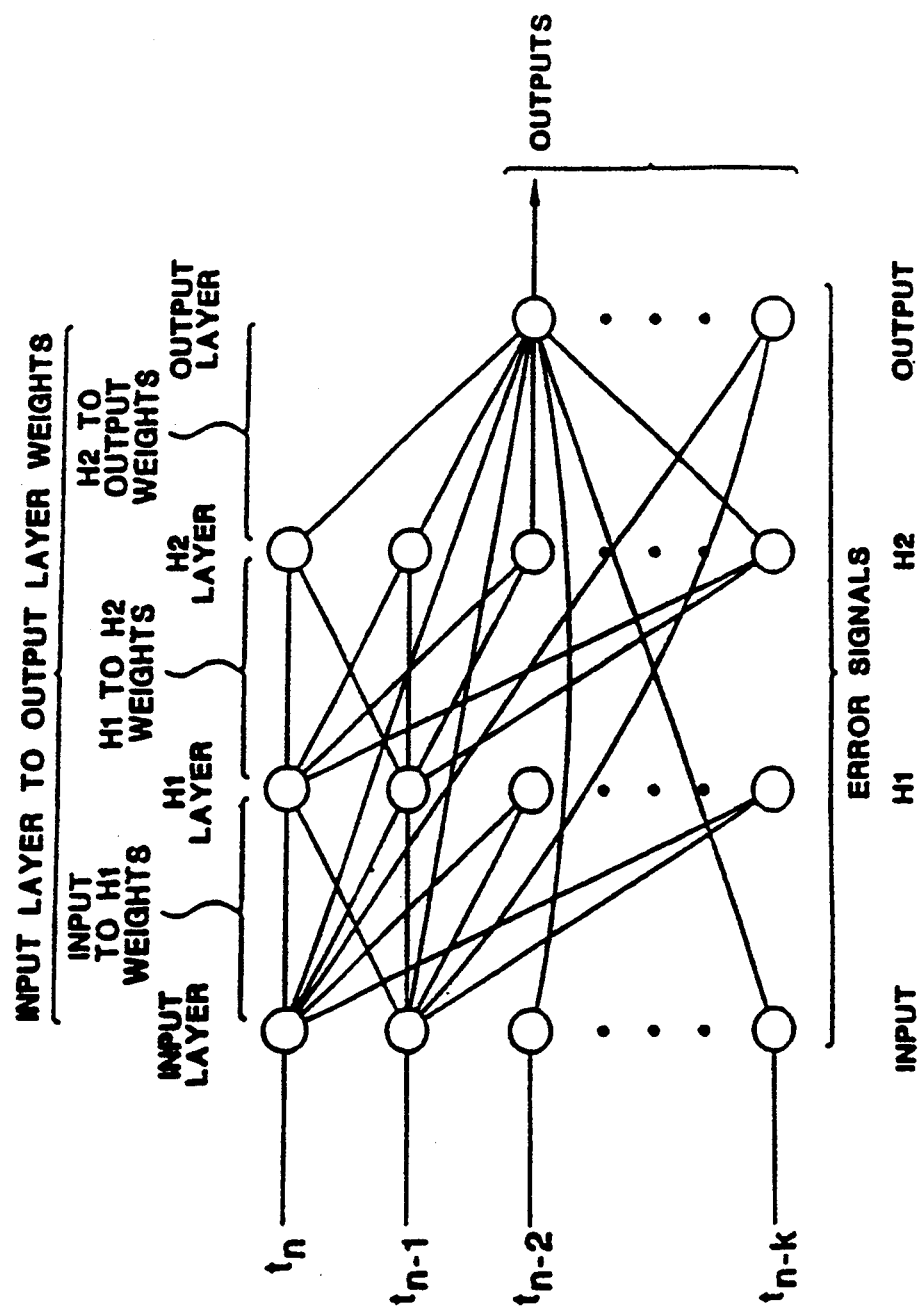

FIG. 10C is a diagram of a four-layer neural network of the type utilized within the high-speed neural network parallel processors of FIG. 8, and as either the neuroemulator or neurocontroller of FIGS. 1D, 10A, and 10B.

Figure 11A:
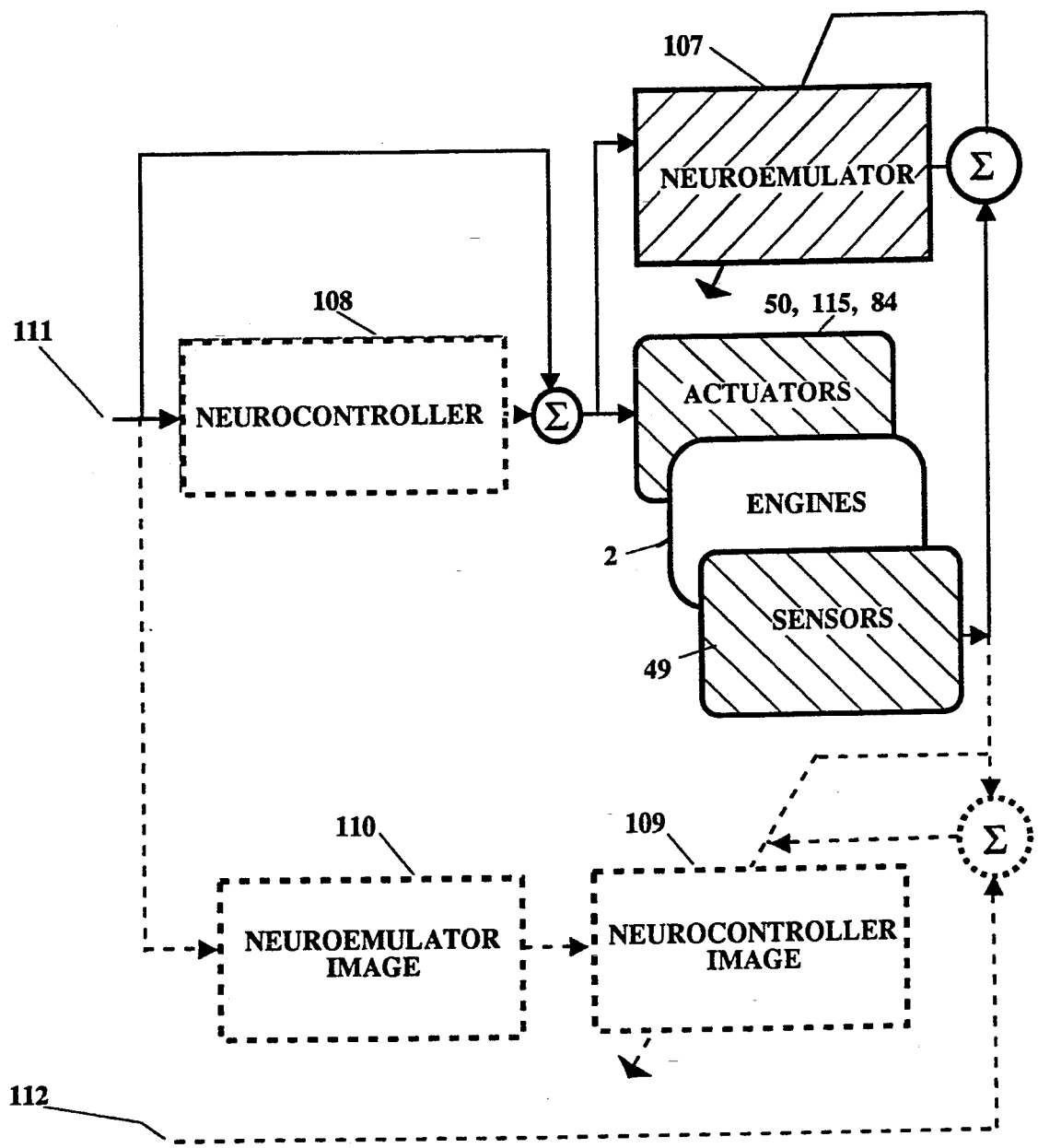

FIG. 11A is a schematic illustrating the emulator network of the present invention.

Figure 11B:
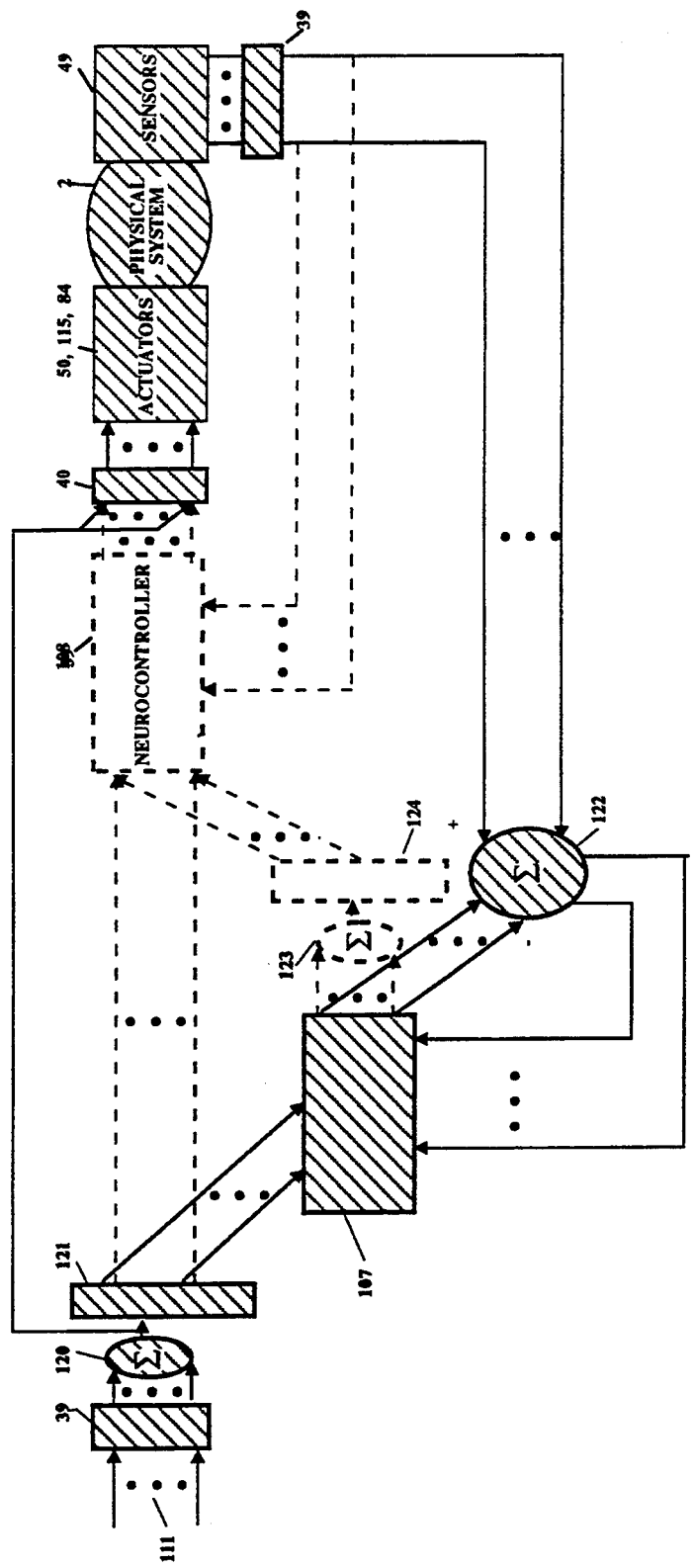

FIG. 11B is a schematic diagram showing the emulator input signal.

Figure 11C:
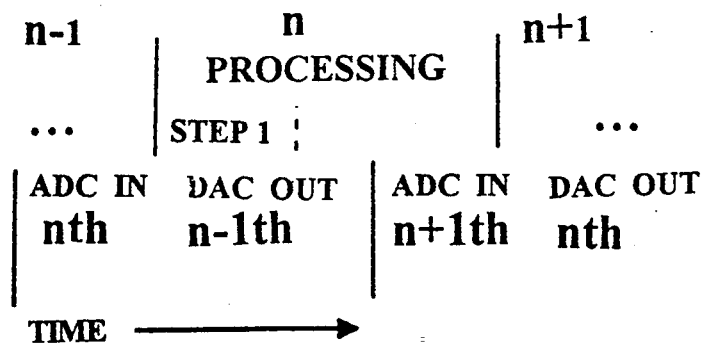

FIG. 11C illustrates the timing during one sample epoch of neuroemulator training.

Figure 12D:
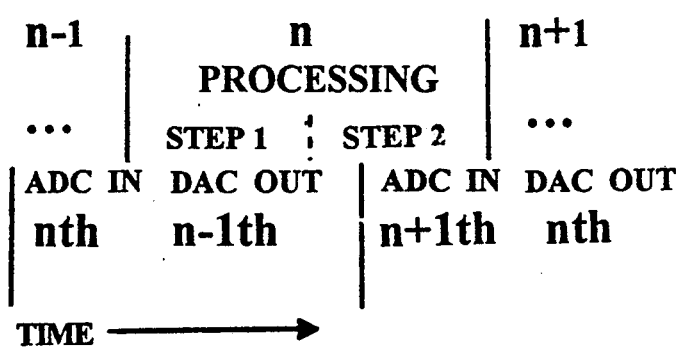
Figure 12A:
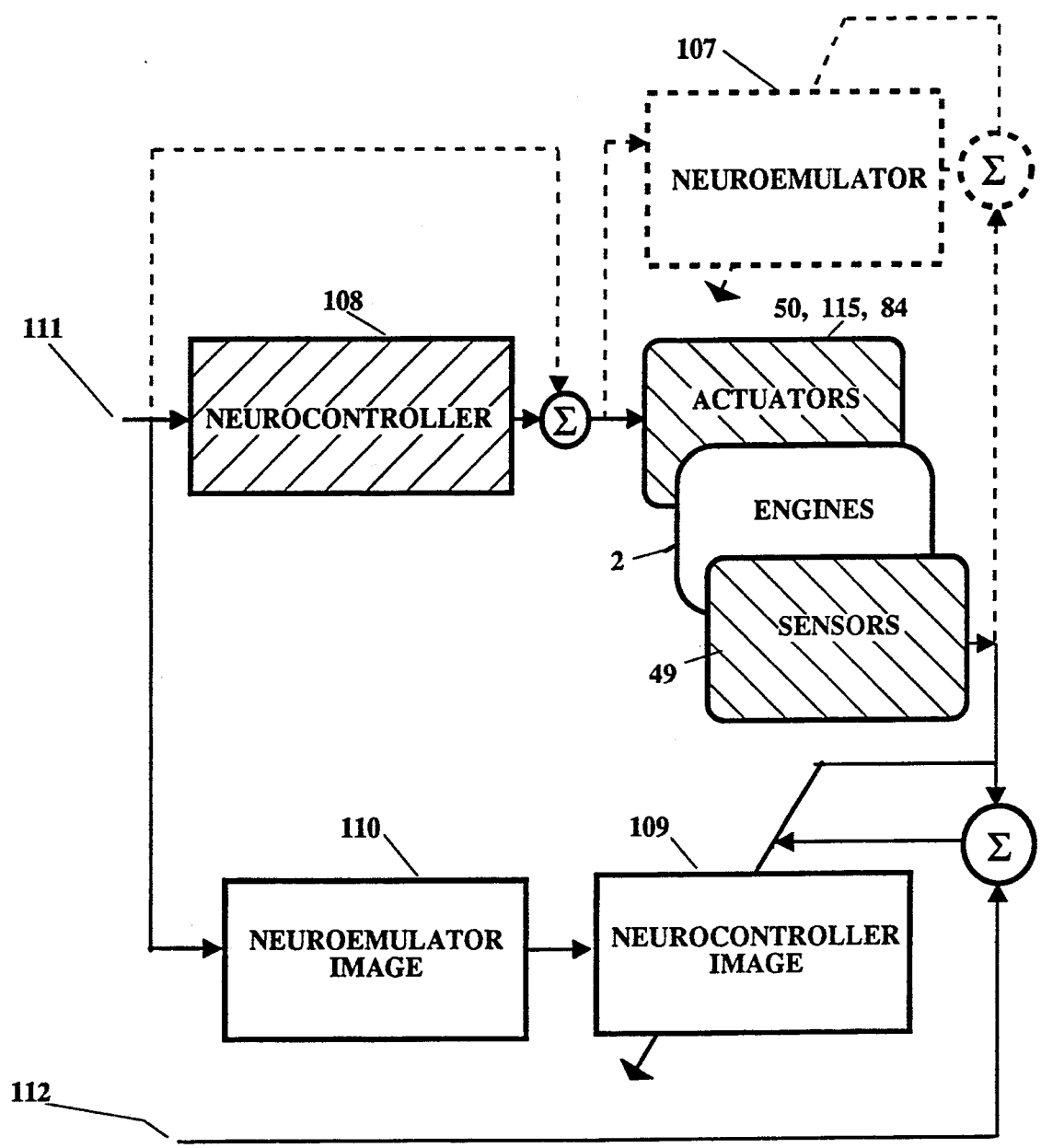

FIG. 12A is a schematic block diagram illustrating the training of the neurocontroller of FIG. 10B.

Figure 12B:
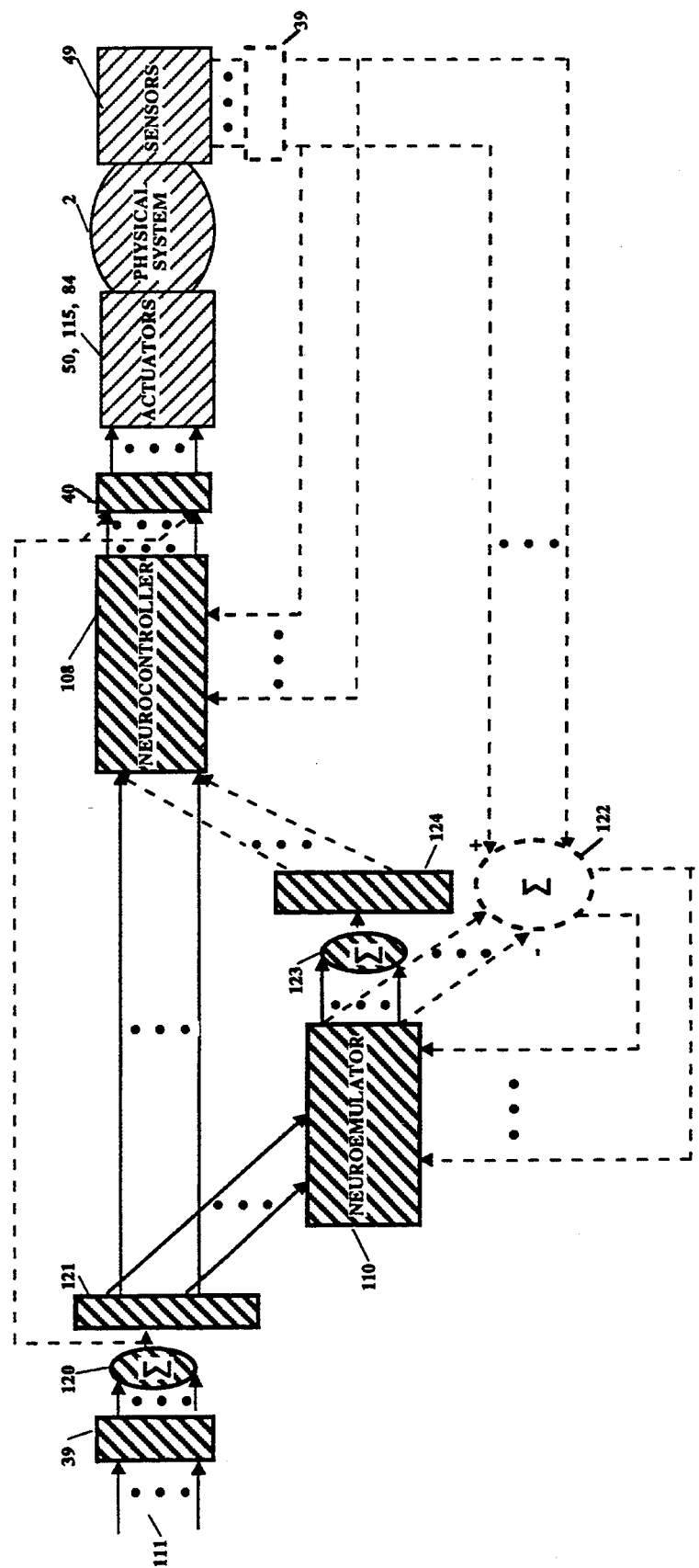

FIG. 12B depicts the trained neuroemulator input signal sequence.

Figure 12C:
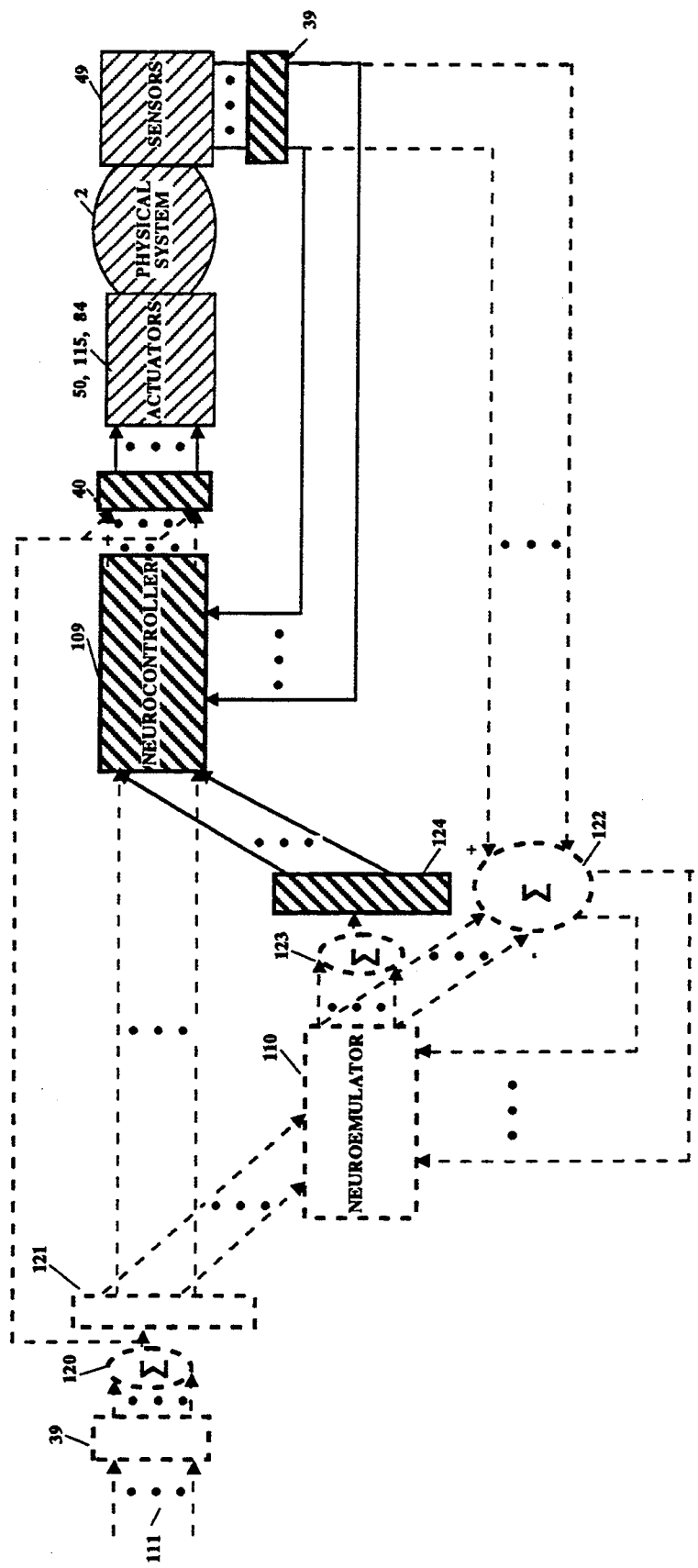

FIG. 12C is a schematic depicting the training of the neurocontroller.

FIG. 12D illustrates the timing involved with the events duping one sample epoch of neurocontroller operation.

Figure 13C:
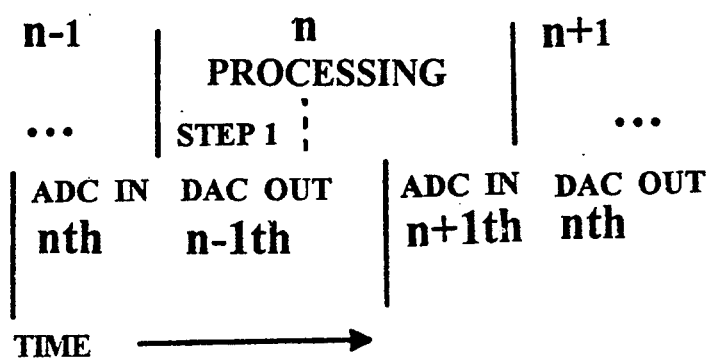
Figure 13A:
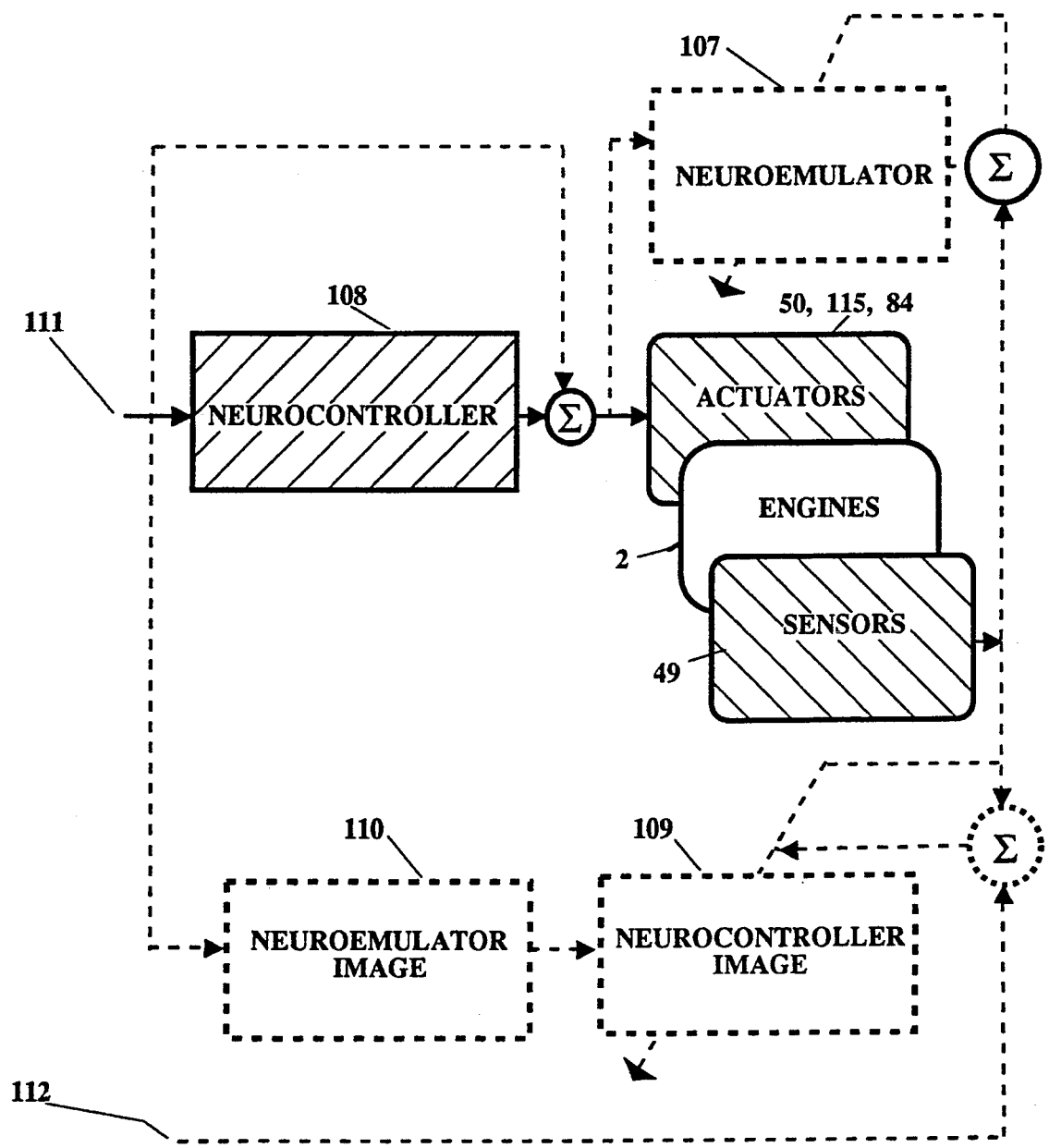

FIG. 13A further depicts the emulator network of the present invention.

Figure 13B:
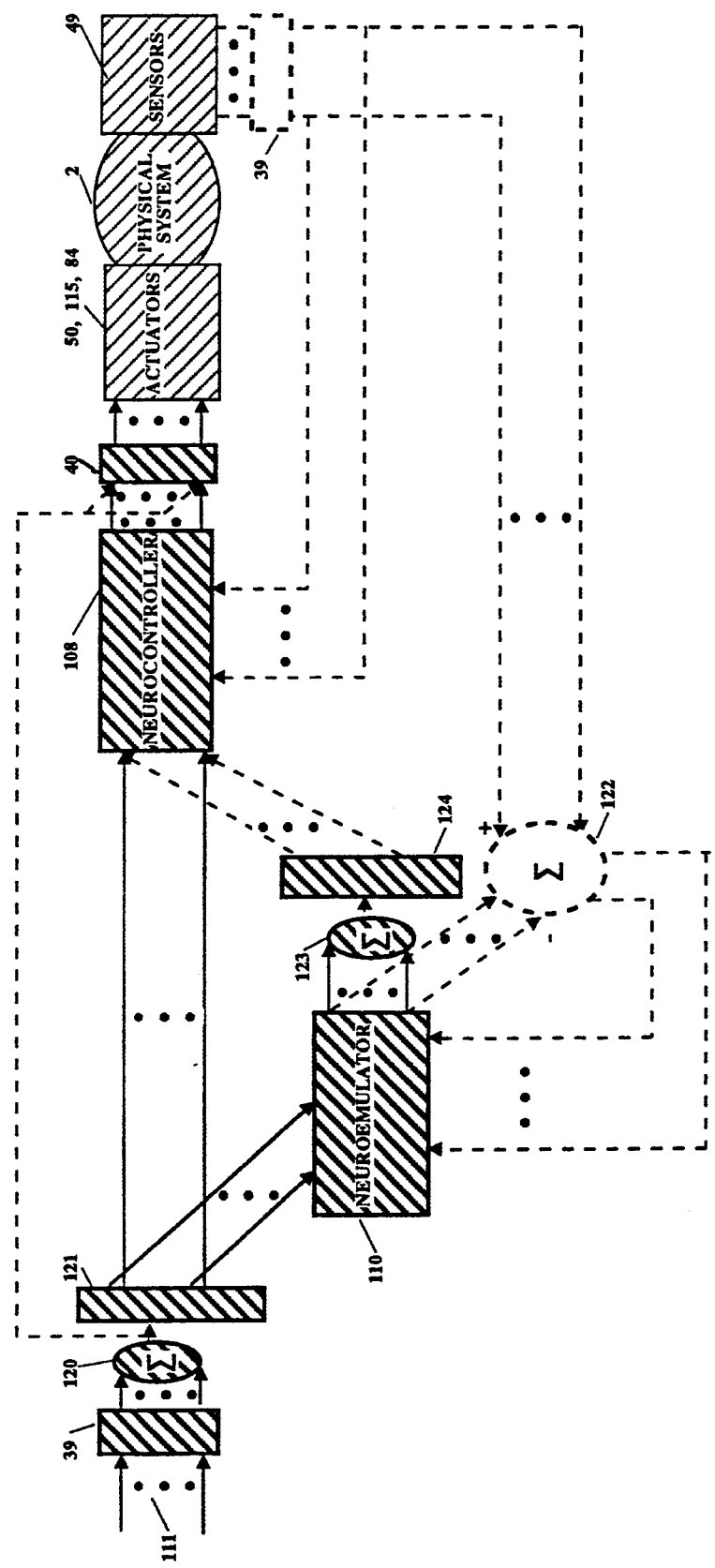

FIG. 13B is a schematic depicting overlapped feedforward operations of the present invention.

FIG. 13C further depicts the timing in the present invention.

DETAILED DESCRIPTION OF A PREFERRED EMBODIMENT

FIG. 1A is a schematic diagram of a typical jet engine nacelle 114. The nacelle consists of cowl 9 and inlet duct 13, the engine cowl panels 10 and bypass duct 14, and the exhaust duct 15 that includes tailpipe extension 11 and the thrust reverser and tailpipe 12. The nacelle and engine schematic shows the zones for the installation of noise source Sensors 7, internal error Sensors 5, external error Sensors 4 and 8, and canceling Actuators 6. FIG. 1A also illustrates the positions of the turbofan 1 and the engine 2 within the Nacelle 114.

FIG. 1B shows a schematic diagram of the primary turbofan engine-produced acoustic noise sources. The rotating turbine blade-generated noise region 21 includes the noise generated by the combustion chambers 19 and the noise generated by the power turbines 20. The noise in region 21 combines with the turbofan blade-generated bypass noise in bypass air 17. The acoustic noise sources 21 and 17 combine to become the rearward-radiated internal engine-generated exhaust noise in exhaust noise zone 22. This noise 22 combines with the rearward-radiated external acoustic noise in shear zone 23 generated in the shear mechanisms between the exhaust gases and the ambient atmosphere. The inlet acoustic noise in source zone 24 consists of the forward-radiating acoustic noise generated by the rotating turbofan blades 1 and the rotating compressor blades 18.

FIG. 1C is a schematic diagram illustrating the process of acoustic wave destructive interference. FIG. 1C shows the noise source waveforms as they would appear at a plurality of measurement locations 26. The noise suppression system uses these measurements to control a plurality of 'anti-noise' generators 50, 115, 84 (see FIG. 2A) located in canceling Actuator zones 6 to produce canceling acoustic noise 'waves' 27 as shown in FIG. 1C. FIG. 1c shows that these waves collectively interfere with the existing acoustic noise 'waves' 26 at the plurality of measurement locations in the error sensor zones 5. The result of this action markedly reduces the amplitudes of the internally-produced acoustic 'waves' 29 that continue to propagate out of the exhaust 15 or out of the inlet 14. When this process is extended to an additional plurality of measurement locations 8 and 4, external to the engine, additional noise reduction results.

FIG. 1D illustrates a method and apparatus for providing canceling acoustic waves propagating through an elastic medium such as air. Acoustic error Sensors 49, (see FIG. 2A) such as microphones, generate audio varying output signals representative of the acoustic waves that exist at the noise source Sensor locations 31 and 33 in zones 7 and the error Sensor locations 30, 32, 34 and 38 in zones 5, 4 and 8. These signals provide inputs to a neurocontroller 113 that learns to generate audio varying output signals that in turn cause acoustic generators 50, 115 and 84 (see FIG. 2A) at the canceling Actuator locations 35, 36 and 37 in zones 6 to produce acoustic waves that are mirror images of the engine-generated acoustic waves measured at error Sensor locations 30, 32, 34 and 38 in zones 5, 4 and 8. The generated acoustic waves interfere with the existing acoustic noise waves at the error Sensor locations 30, 32, 34, and 38 in zones 5, 4, and 8. The final result is wave interference and cancellation. The neurocontroller means 113 will continue to adapt its output signals 35, .36, 37 such that the audio signals measured by the microphones in sensor zone 49 (see FIG. 2A) are always minimized. The net result of the invention is the reduction in the measured sound levels at the microphone locations in both the internal error Sensor zones 49 and the external error Sensor zones 69.

FIG. 1D illustrates the application of the invention to one or more gas turbine (turbofan) engine assemblies 114. A turbofan engine 2 creates thrust by moving air from the surrounding air medium through the engine, compressing it 18 mixing fuel with it, and igniting the fuel air mixture to produce a hot exhaust gas 19. The hot gas rotates the power turbines 20, that, in turn, rotate the turbofan 1 and compressors 18. The hot exhaust gasses mix with the cooler bypass air 21. Finally, the exhaust mixture 22 moves out of the engine 2 through the exhaust tailpipe 15. Thrust forces produced by these processes on the engine move the aircraft forward. The engine generates acoustic noise due to the aforedescribed processes. In addition, the turbulent boundary layer between the hot exhaust mixture and the relatively 'undisturbed' cooler atmosphere produces acoustic noise 23.

These two sources of acoustic noise combine to radiate into the far field (that is, far from the engine). Acoustic noise generated by the compressing blades 18 radiates forward out of the inlet duct 13. Similar acoustic noise 17 is radiated rearward into the bypass duct 16 from the actions of the bypass fan 2. The inlet's forward-radiated noise 24 also combines with the exhaust's rearward-radiated noise 22 and 23 at locations far (far field) from the engine. Multiple engines combine to increase the radiated far-field noise.

One or mope acoustic sources (usually actuators 50, see FIG. 5A, air stream modulators 115 (see FIG. 4A), or piezoceramic actuators 84 (see FIG. 6A) are the means to create sound. FIG. 1A, 1D and 2A show where the Actuators ape located, namely in the actuator zones 6 of the engine exhaust 15, inlet 13 and bypass ducts 16. FIG. 1D depicts the electrical drive signals 35, 36 and 37, that ape furnished to the Actuators 50, 115 and 84 from the Controllers 113. The controllers 113 condition the drive signals to match the electrical characteristics of the Actuators 50, 115 and 84. FIG. 10 shows that the Actuators at locations i, i and k, and so forth in zones 6 adaptively produce canceling acoustic waveforms 27 that interfere destructively with the engine generated acoustic waveforms 26 at either an internal external location 'M' in zones 5 of the error Sensors 49 (see FIG. 2A). This destructive waveform interference reduces the sound levels measured by the error Sensors 49 at location 'M'. This process reduces the sound levels internal to the engine and realizes a reduction in the external perceived sound levels.

The means to measure sound ape preferably of two categories: source Sensors in zone 49 (usually dynamic pressure sensor microphones) to measure the normal engine generated sound; and error Sensors in zone 49 (usually dynamic pressure sensors microphones) to measure reduced sound.

The source Sensors 49 ape 'upstream' from the Actuators 50, 115 and 84 and the error Sensors 49 are 'downstream' from the Actuators .50, 115 and 84. "Upstream" refers to closer to the sound source 1 and 15 than the Actuators and "downstream" refers to further from the sound source 1 and 15 than the Actuators. The term Sound source refers to the inlet duct/compressor bypass fan end 13. Sound source also refers to the turbine exhaust/bypass/duct/tailpipe/thrust reverser end 15. FIG. 1A, 1D and 2A show typical sound source locations.

As seen in FIG. 1B and 2A, the turbofan engine 2 generates acoustic waves propagating forward from its air inlet 13, propagating rearward from its exhaust outlet 15, and propagating outward from the engine's vibrating cowling (nacelle) structure 3. The processes of compressing the air entering the inlet by the rotating bypass fan blades 1 and the successive stages of rotating compressor blades 18 generate the acoustic waves propagating from the inlet 13.

Acoustic waves generated at the inlet propagate rearward through the turbofan engine's air bypass duct 16. These acoustic waves also propagate rearward through the air compressor inlet duct 18. They are combined with the acoustic waves generated by each successive compressor stage. This complex acoustic field enters the gas generator ducts 19, combines with the complex acoustic fields generated by the combustion processes and enters the power turbines 20 and exhaust duct 15. These two sets of complex acoustic waves recombine at the exhaust/tailpipe end of the engine and propagate rearward out of the tailpipe 11 and 12. The exhausted acoustic waves 21 combine with acoustic waves generated by the shear mechanisms created at the boundary between the relatively cool ambient air medium and the hot moving exhaust gases 23.

In a preferred embodiment, each engine has a plurality of installed Actuators. FIG. 20 illustrates typical Actuator 50 locations 35 at the exhaust end of the engine 15 along lines 2—2 of FIG. 2A. FIG. 2H illustrates typical actuator 50 locations 37 at the inlet end 13 of the engine along lines 7—7 of FIG. 2A. FIG. 2G illustrates typical actuator 50, locations 36 on the bypass duct 16 portions of the engine along lines 6—6 of FIG. 2A.

FIG. 2D is a typical cross-section of an air modulator actuator horn along the lines 3—3 of FIG. 2A. The horn section 53 of the air modulator serves to increase the sound levels of the air modulator 51. The horn 116 provides impedance loading at the throat 70 of the horn to enhance low-frequency performance. And, the horn section matches the impedance of the ambient bypass air flow at the mouth 71 of the horn. FIG. 2E is a typical cross-section of an air modulator actuator driver 51 and plenum 52 along the lines 4—4 of FIG. 2A and 4B.

The horn mouth attaches to an entry hole in the bypass duct wall by a flange 72 (see FIG. 4B). The plenum 52 attaches by a pipe manifold 54. The pipe manifold 54 attaches to a source of high pressure air. Appropriate bleed ports(s) on the engine's compressor stages provide the sources for high-pressure air. The only stringent requirements are that the compressed air be very clean and the plenum 52 pressure must be at least twice as high as the ambient bypass duct 16 pressure. Thus, the throat 70 of the horn 116 serves as the exit from the high pressure plenum 52 and air modulation. And, the mouth of the horn 71 serves as the entrance back into the bypass duct 16. Each engine has a plurality of air modulator actuators 115.

Each engine has a plurality of internal-to-the-engine Sensors locations 30, 31, 32, 33 and 34 are shown in FIG. 2A. The Sensors 49 in the exhaust tailpipe 15 and inlet 13 provide the error signals to the neurocontroller 113. The neurocontroller 113 optimizes the generation of canceling acoustic waves 27 to improve the interference between the internal, controlled, acoustic wave generation and the internal, engine generated acoustic waves 26. These signals fuse with additional near-field error Sensor signals 49 at locations 38 to assure far-field noise reductions. FIG. 2B illustrates typical sensor locations 34 at the exhaust end 15 of the engine along lines 1'1 of FIG. 2A. FIG. 2I illustrates typical sensor locations 30 at the inlet end 13 of the engine 6 line 8—8 of FIG. 2A. FIG. 2F illustrates typical sensor locations 21, 32 and 33 on the bypass duct 16 portions of the engine along lines 5—5 of FIG. 2A FIG. 3 is a plan view of a typical turbofan aircraft. FIG. 3 shows typical external-to-the-engine Sensor 49 locations (near field) 38 on the fuselage 65, wings 67, tail 68, and stabilizers 66. These error Sensor signals 38 and the internal error Sensor signals 30, 32, and 34 combine to improve the noise reduction performance in the near field external to the engines A plurality of external error Sensors 49 are installed on each aircraft. The error Sensors 49 may be common to one or more engines.

FIG. 4A is a cross section view of typical air stream modulator 115 and a horn 116 installed on and within the bypass ducts 16. This device is one type of acoustic Actuator that provides cancellation acoustic waves 27. An air stream modulator 115 requires a flow of compressed air. To operate efficiently, pressure in the plenum 52 are at least twice as high as the ambient bypass duct 16 air pressure. The higher the mass flow the greater the sound output. Therefore, it is an efficient device for operation on a turbofan engine 2 where enough air flow is available. Since most of the needed acoustic energy is provided by the compressor stages, the electrical input power required to drive the modulator's armature 47 is a minimum. FIG. 4A is a cross-section view of a typical air modulator 115 and horn 116. FIG. 4A illustrates the relationships of high pressure supply 54, high pressure plenum 52, armature 47, stator 48, driver 51, acoustic horn 116 and attachment mechanisms 72.

The acoustic exit horn 116 couples the acoustic wave energy to the air stream at the horn mouth 71. The air supply plenum 52 sustains a pressure head within the modulator 115. FIG. 4C is a cross-section view along the lines 4—4 of FIG. 2E that illustrates the concentric relationships of the air modulator's cylindrical armature 47 and stator 48. The driver 51 is a stiffness-controlled high-force, large-displacement electrodynamic actuator, or the equivalent. That is, it operates in the stiffness-controlled region of its response spectrum. FIG. 4B is a top view of an embodiment of an air modulator 115 and acoustic horn 116.

The plenum 52 provides a supply of air at sustained pressure. The driver 51 vibrates the armature 47 such that the moving slots in the armature 47 move in relation to the stationary slots in the stator 48, This motion modulates the openings between the two opposing sets of slots. Changes in opening size modulate the air flow, which in turn, modulate the pressures at the horn throat 70; which results in the controlled modulation of the pressure generated acoustic waves that propagate from the throat 70 of the horn 116 to its mouth 71. The horn geometry is designed to provide an impedance load at its throat 70 that improves its low-frequency performance. This extends the useful bandwidth of the air modulator 115. The exit horn 116 provides an impedance match between the horn mouth 71 and the air stream in the bypass duct 16, As a result, the generated sound level increases and the acoustic transfer efficiency to the ambient air stream improves, Cancellation occurs through the mechanisms of wave interference. That is, the generated acoustic waves carried by the bypass air stream mix with the acoustic waves produced by the bypass air flow 17 and exhaust gas flow 21.

FIG. 5A and 5B, respectively are plan views of typical installations of high-intensity acoustic loudspeaker Actuators (speakers) 50 in the inlet duct. 13, the bypass ducts 16, and the forward end of the tailpipe 15. This device 50 represents another acoustic Actuator type, This Actuator provides a source of cancellation acoustic waves. Each separately controlled speaker requires a cooling air flow 16 around its driver mechanism 51 and heat exchanger 76. A speaker requires electrical energy in order to provide acoustic energy. Although speakers are not very efficient, they provide a broad range of high frequency responses. FIG. 5C is a cross-section view along lines 11—11 of FIG. 5A that illustrates typical relationships between driver 79, 'former' and 'cone' assembly 77, frame 75, and cooling heat exchanger 76. The motion of the driver voice coil 79 drives the former and cone assembly 77. The 'cone' 77 couples the mechanical motion to the air medium 13, 15 and 16 and produces acoustic waves 27. Typically, an audio signal 35, 36 or 37 provided to the voice coil 79 causes it to vibrate within the magnetic field that exists between the permanent magnets 80 and the driver core and pole piece 81. This vibration, in turn, vibrates the 'cone' 77 and couples the audio signal 35, 36 or 37 to the air medium 13, 15 or 16 in the form of an acoustic wave 27.

FIG. 6A is a cross-section view of a typical high-force piezoceramic Actuator assembly 84. A piezoceramic Actuator assembly 84 is made up of a mosaic of piezoceramic Actuator blocks 82. These blocks 82 produce forces and motions through piezoelectric activity when a voltage is applied across opposite faces of the blocks 82. Typical installations include: the inlet duct 13, the bypass ducts 16, the struts between the bypass ducts and the engine cases 64, the stator blades of the bypass fan 56, and the stator blades of successive compressor stages 18. Piezoceramic Actuator assemblies 84 can bend and stretch panels 55 to Actuator assemblies 84 can bend and stretch panels 27. FIG. 6B is a cross-section view along lines 12—12 of FIG. 6A that illustrates the piezoceramic Actuator assembly 84 installed to impart motion to a panel 55.

FIG. 2J is a cross-section view along lines 9—9 of FIG. 2A that illustrates the installation of piezoceramic Actuators assemblies 84 mounted on both sides of a cylindrical engine duct 55. Applying the same in-phase audio voltage signal to both sides of the Actuator assembly 84 produces stretching of the panel 55. Applying the same out-of-phase audio voltage signal to both sides of the Actuator assembly 84 produces bending of the panel 55. Piezoceramic Actuators 82 applied to only one side of a panel 55 produce combined stretching and bending. The flexing panels act like speakers hence they will produce sound. Piezoceramic Actuator assemblies 84 produce large forces, however the motions are small. Piezoceramic Actuators produce high acoustic levels in the medium to high frequency ranges.

FIG. 2A includes typical Sensor installations. FIG. 7 is a plane view of one of these installations along the lines 1—1, 5—5, and 8—8 of FIG. 2A. The Sensors measure the analog fluctuation of acoustic pressures and vibration versus time acting on its sensitive face 86. The frequency sensitivity of the Sensors is at least as wide as the bandwidth of engine noise. Their amplitude sensitivity has enough dynamic range to measure the full variation of ranges of flight dynamic and environmental conditions encountered over the engine's frequency response bandwidth. The Sensor 49 consists of the active element 86, mounting block 90, gas seal washer 89, jam nut 87 and electrical connector 88. FIG. 7 shows the Sensor assembly 49 attached to a panel 55.

FIG. 8 is a simplified block diagram of the typical acoustic noise reduction system instrumentation 119 installed on an aircraft. Sensor 49 generates source and error signals. Sensor Signal Conditioning amplifiers 93 provide impedance matching, charge-to-voltage conversion, and other conditioning of these signals. Limiting the frequency range and adjusting the overall gain is the function of the input programmable gains and filters 95. An analog-to-digital conversion subsystem 39 provides for conversion of these analog input signals to digital samples. Synchronizing the sampling rate to the engines rotational cycle reference signal 45 is the job of the rotational speed synchronizer 101. This unit 101 maintains a constant number of samples per rotational cycle regardless of engine speed. Another way of stating this process is that the digital samples now represent the signals in the 'revolution' domain synonymous to the 'time' domain.

FIGS. 9A, B, and C comprise a series of diagrams that illustrate how the Controller is synchronized to a reference signal 45, such as a once-per-revolution 'keyphasor' reference on a rotating machinery shaft. FIG. 9A shows a signal that varies from 1 Hz to 2 Hz to 1.4 Hz in the time domain on the left side of the figure. The right side of FIG. 9A shows how these waveforms correspond to the first order in the order domain when the sampling rate is eight samples pep cycle fop each example. In the frequency domain these components would appear at 1 Hz, 2 Hz, and 1.4 Hz, Pespectively, when the sampling rate was a constant eight samples per second for all three examples.

Figure 9B:
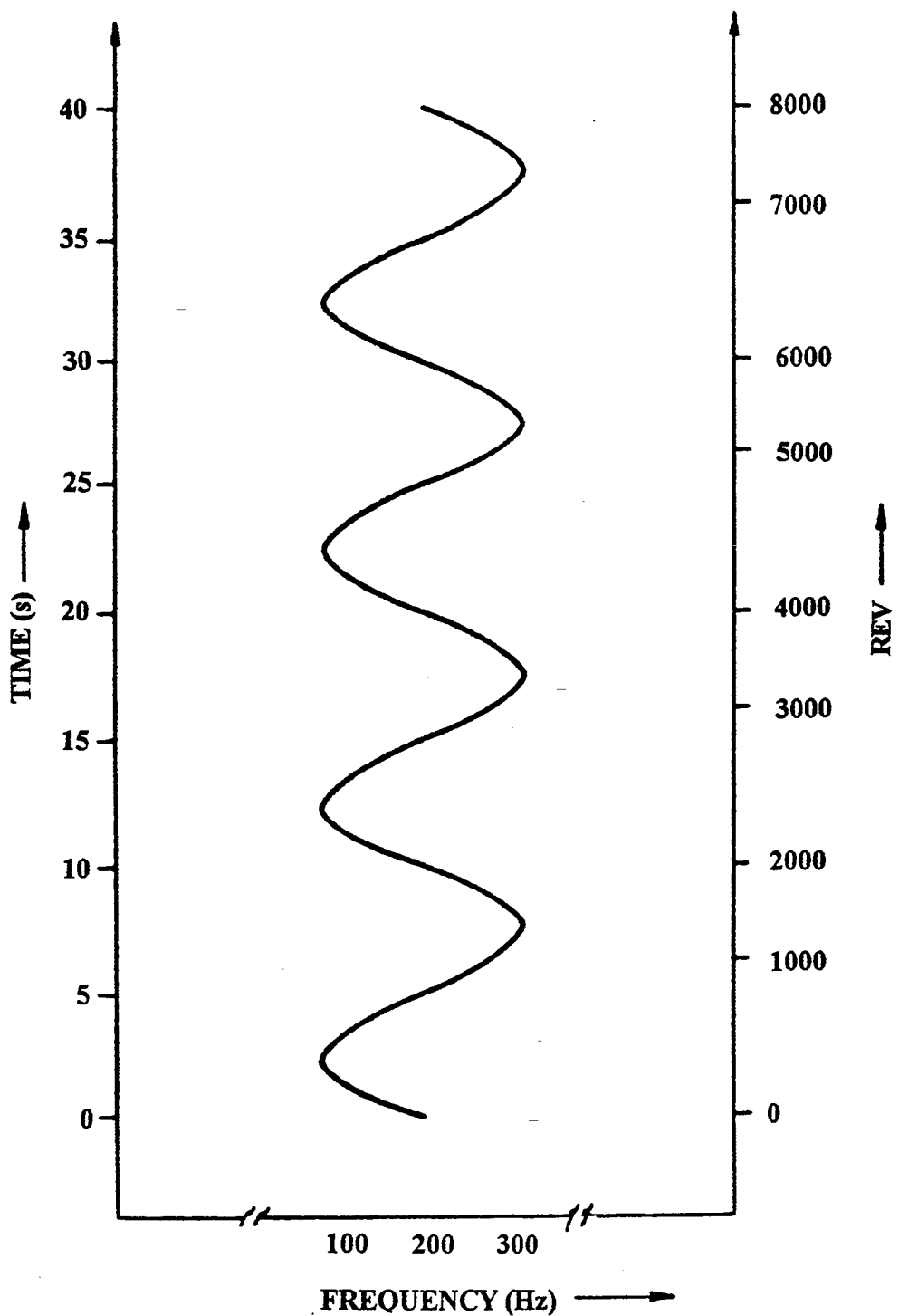
Figure 9C:
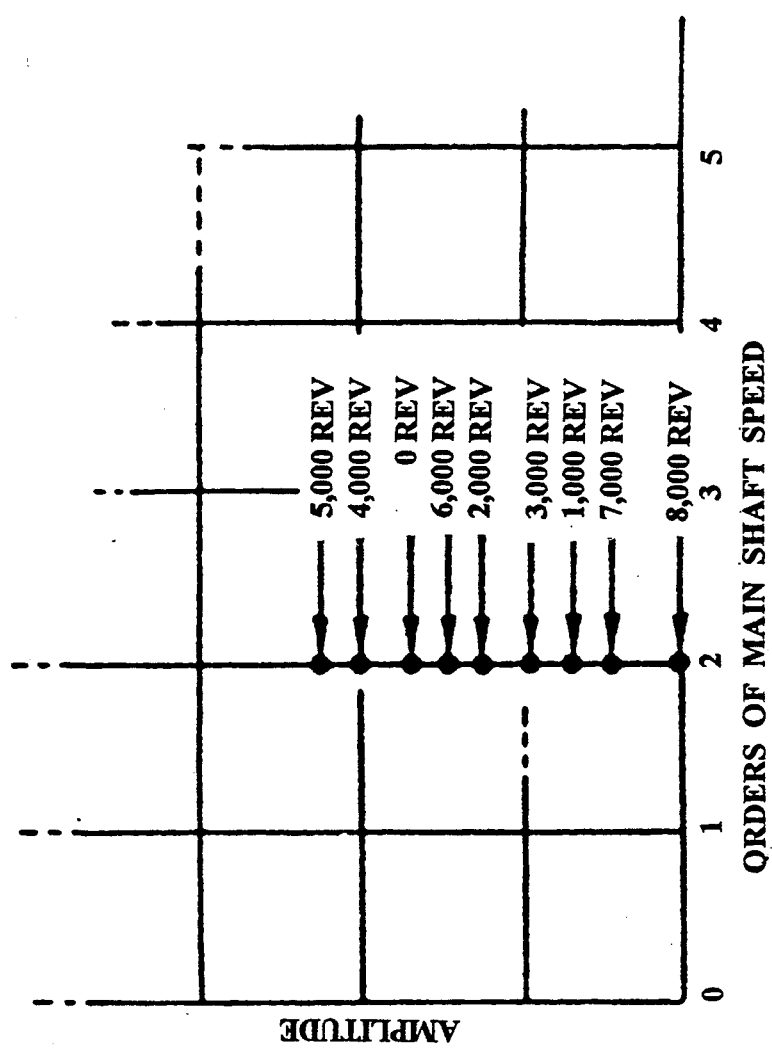
Figure 9D:
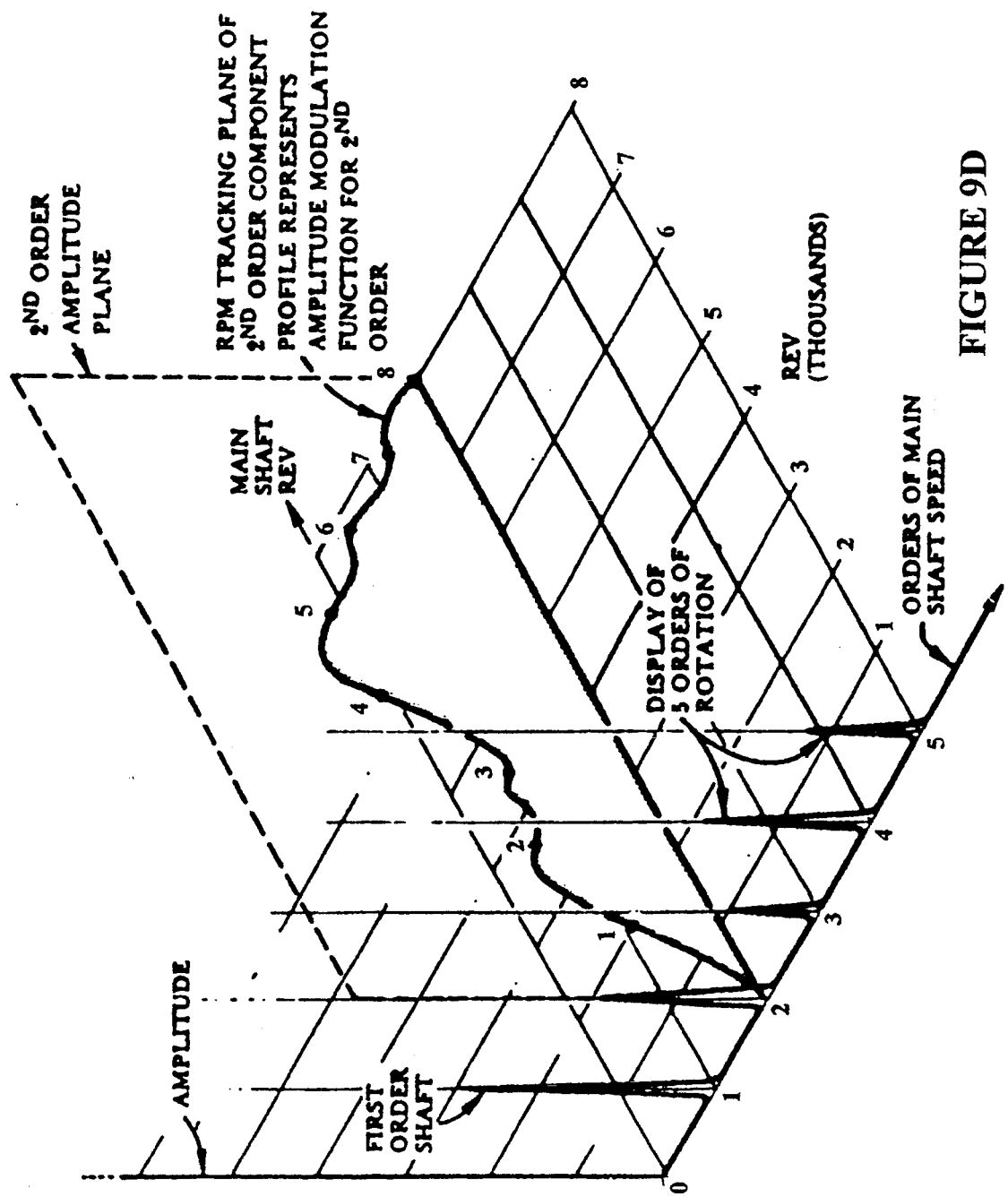

Fig, 9B illustrates the correspondence of time and revolutions fop a single rotating frequency component when the speed of rotation is varying in time. FIGS. 9C and 9D show order-tracking in the order domain using synchronous sampling at 10 samples per revolution. Note that the first five harmonics of the rotational speed ape stationary in the order axis. Also, note that their amplitudes vary in the amplitude axis as speed varies, This feature is illustrated by the second order in FIGS. 9C and 9D.

On a typical turbofan engine, the rotational speeds are available as N1 and N2. N1 and N2 ape tachometers that measure the speeds of the two shafts of the turbofan engine. Synchronizing the neurocontroller's operations to either N1 or N2 means that the inputs 31 and 33 errors 30, 32, 34 and 38 and outputs 35, 36 and 37 to/from the neurocontroller 112 will be sampled at an integer multiple of either N1 or N2. Since the sampled data rate controls the neurocontroller operation, the neurocontroller process synchronizes to this reference function 45. Tachometer-controlled sampling of the input source 31 and 33 and error 30, 32, 34 and 38 signals converts these signals from the analog time domain to the digital revolution domain. A tachometer-controlled operation means that the Controller operation is proportional to a multiple of the machinery rotational speed. Synchronization transforms the control topology from the traditional time and frequency domains to the corresponding rotational domains of 'revolutions' and harmonic 'orders'. The neurocontroller places emphasis on control of rotation-related acoustics/vibration and becomes more responsive to their variations. The conversion of digital outputs 35, 36, and 37 back to analog are tachometer-controlled. This digital-to-along conversion process returns the digitally-sampled output data from the revolution domain back to the time domain.

The current filtered-x, multiple neural network controller architecture eliminates shortcomings of earlier work, (Bozich, D. J. and MacKay, H. B., *Neurocontrollers Applied To Real-Time Vibration Cancellation At Multiple Locations*, Conference on Recent Advances In Active Control Of Sound And Vibration, V.P.I., Apr. 15–17 1991) using a single neural network with a feedforward architecture and the back propagation (BP) learning algorithm. The architecture used here is derived from the "filtered-x" adaptive controllers. A significant difference between adaptive Neurocontrollers and conventional adaptive controllers is the utilization of BP neural networks in place of the more conventional LMS networks.

A neural network is an arrangement of interconnected units modelled after similar structures in the nervous system of living organisms. The connections between the units are each governed by a modifiable weight. Each neuron analogue is associated with a number termed its activity. Each unit converts patterns of incoming activities into outgoing activities that are sent to other units. This is accomplished by multiplying each incoming activity by the weight of the connection and then summing the weighted inputs to get a total input, An input-output function transforms the total input into an outgoing activity. Thus the performance of the neural network depends on both the weights and the input-output function specified for the units. Typically there ape three layers of units termed the input, hidden, and output layers. The activity of the units in the hidden layer ape determined by the activities of the input units and the weights on the connections between them and the hidden units, The activity of the output units depends on the activity of the hidden units and the weights between the hidden and output units. The advantage of the neural network is that the hidden units representation of the inputs is not pre-programmed but is adjusted during a process called training. Training consists of exposing the neural network to a pattern of activities and adjusting the weight of each connection so that the neural network produces a mope acceptable output response, FIG. 10A is a block diagram of the Neurocontroller 112, The Controller 112 incorporates a neural network based version of the filtered-x adaptive controller. The neuro-controller uses multiple networks, namely, an emulator network ('Neuroemulator') 107 and a controller network ('Neurocontroller') 108. The Neuroemulator 107 develops an on-line model of the dynamics of the physical system. The physical system includes actuators 50, 115, 84 and sensors 49. This emulation of the physical system provides the system identification necessary to enable the neurocontroller 112 to span the required operating frequency and amplitude ranges. Next, a copy of the trained Neuroemulator 110 placed in front of the controller network 109 provides adaptive training of the Neurocontroller 112. A current copy of the trained controller network 108 placed in front of the physical system effectively preprocesses (a feedforward operation) the input signal 31 and 33 such that the measured errors 30, 32, 34 and 38 are minimized.

This approach minimizes the instabilities due to the phase delays of the error signals returned to the controller 112. The outstanding feature of the filtered-x approach is that the process of adapting (training) the Neurocontroller 112 becomes the last operation instead of the first operation. Therefore the delay between error signals 30, 32, 34 and 38 and the neuro-controller output signals 35, 36, 37 is minimal. For a given Neurocontroller 112 output response, the resultant error signal naturally delays through the actions of the physical system's delay between the transfer functions. The myriad transfer functions include the cross-transfer functions between the cancellation Actuators 50, 115, and 84, the acoustic and structural responses, and the error Sensors 49. The cross-transfer functions between the acoustic source Sensor(s) 31 and 33 and the acoustic error Sensors 30, 32, 34, and 38 are products of the Controller transfer function and the actuator/acoustic/structure/sensor transfer functions. Therefore, measures of the effects of the Controller 112 on canceling the effects of the system are delayed. For a moderately linear system, it would be possible to switch the order of the Controller and the actuator/acoustic/structure/sensor operations and obtain the same overall transfer function.

To achieve this switch in the order of Controller 113 and system operations, the actuator/acoustic/structure/sensor transfer functions are first learned by the emulator network as shown in FIG. 11A. During this emulator training mode, the controller network 108 is disabled and bypassed in order to feed the acoustic source input 111 directly to the emulator 107 and the cancellation actuators 50, 115, and 84. FIG. 11B shows the emulator input signal consisting of the digitized 39 and summed 120 (fused) actuator input signals (source sensor inputs). The summed input signal 120 is placed into a ring buffer on shift register 121 that contains a shifted sequence of past input signal samples. This sequence of samples serves as the parallel input layer for the neuroemulator 107. The emulator's outputs are compared 122 to the digitized 39 error sensor 49 responses to produce difference signals, that is, errors for training the emulator. The emulator training continues until all differences are reduced to zero, or at least minimized.

FIG. 11B illustrates the timing involved with the events during one sample epoch of neuroemulator training. The input signals are digitized (ADC) 39 and summed 120 to form the nth sample of the input signal 121 or the neuroemulator and the summed input signal is converted to parallel analog signals (DAO) 40 to drive the actuators 50, 115 and 84, The neuroemulator performs a feed forward operation of the nth set of the shifted input signal sequence through the network and obtains a set of outputs. The nth set of error sensor response signal samples that were digitized 39 at the same time as the input signals are compared to these network outputs to obtain differences that serve as errors to be backpropagated through the network to adjust the network weights for the next n+1 th sample epoch. This training process continues until the differences (errors) reduce to zero or minimize.

When switching from the emulator training mode to the control mode, the controller bypass and the emulator training mode are disabled and the controller output signals 108 are enabled.

As indicated in FIG. 10A shows that the trained emulator weights are the emulator image network 110 weights. The emulator image 110 applies the actuator/acoustic/structure/sensor system transfer functions between the acoustic source input signal and the controller image network 109, FIG. 1A shows the trained neuroemulator input signal sequence consisting of the digitized 39 and summed 120 (fused) source sensor inputs. The summed input signal 120 is placed into a ring buffer or shift register 121 that contains a shifted sequence of past input signal samples. This sequence of samples serves as the parallel input layer for the neuroemulator 107. The emulator performs a feedforward operation. The outputs of the emulator image network 110 are summed (fused) and provide the input to the controller image network's ring buffer or shift register 124. The ring buffer or shift register 121 also contains the shifted sequence of the past n−1th input signal samples. This n−1th sequence of samples serves as the parallel input layer for the neurocontroller 108. The controller performs a feedforward operation. The outputs of the controller network 108 are converted to analog signals 40 and drive the actuators 50, 115, and 84. The emulator output sequence contained in the ring buffer or shift register 124 is used to train the controller image network 109. The controller image network trains the weights of the controller network 108 as if the physical System preceded the controller 112, thereby decreasing the phase delays of the measured error signals 30, 32, 34, and 38. During this process, the controller network 108 provides the actual signals to the physical System using the trained weights. The controller 112 requires constant-pressure (DC) compensation loops. Also, high-pass filtering of the output signals of the controller network 108 extract the DC components of these signals.

FIG. 12C illustrates the timing involved with the events during one sample epoch of neurocontroller operation consisting of feedforward operations through both the nth instance of the trained neuroemulator and the n−1th instance of the trained neurocontroller and the training of the nth instance of neurocontroller weights through a process of feedforward and error backpropagation. In advance of step 1 of FIG. 120, as shown in FIG. 12A, the input signals ape digitized (ADO) 39 and summed 120 to provide the nth sample sequence of the input signal 121 for the neuroemulator image 110 and the n−1th sample sequence for the neurocontroller image 108. In step 1, as indicated in FIGS. 12A and 12C, the trained neuroemulator performs a feed forward operation of the nth set of the shifted input signal sequence through the network and obtains a set of outputs that are summed (fused) 123 and placed in the shifted ring buffer or shift register 124. The trained neurocontroller performs a feedforward operation of the n−1th set of the shifted input signal sequence through the network and obtains a set of outputs that drive the actuators. In step 2, as indicated in FIGS. 12B and 12C, the nth emulator output sequence from the ring buffer 124 are the parallel inputs for the feedforward operation of the controller image network 109. The nth set of error sensor response signal samples that were digitized 39 at the same time as the nth set of input signal samples are the errors to be backpropagated through the controller image network 109 to adjust the network weights fop the next n+1th sample epoch. This training process continues until the response sensor outputs (errors) reduce to zero or minimize.

Once the errors minimize, the neurocontroller training is essentially complete. The training can continue to track non-stationary changes in the excitation environment, as shown in FIG. 12A and 12B. If the excitation is steady-state (stationary), the training period can end and the trained controller 113 continues to control as shown in FIG. 13A. FIG. 13A and 13B are the same operations as explained for FIG. 12A and step 1 of 12C, respectively.

Once the errors minimize, the neurocontroller training is essentially complete. The training can continue to track non-stationary changes in the excitation environment, as shown in FIG. 12A–C. If the excitation is steady-state (stationary), the training period can end and the trained controller 112 continues to control as shown in FIG. 13A–B.

The Controller 112 includes the adaptive neurocontroller hardware and software system 112. The controller 113 comprises: a very-high-speed parallel processor 42; program management computer 43; I/0 signals management computer 41 (with analog-to-digital conversion sub-systems 39); digital-to-analog conversion sub-systems 40 (with interfaces to source sensors 31 and 33, error Sensors 49 and. 69, and cancellation Actuators 50, 115 and 84); and support software and the adaptive control and neurocontrol software.

While there have been shown and described and pointed out the fundamental novel features of the invention as applied to preferred embodiments thereof, it will be understood that various omissions and substitutions and changes in the form and details of the device illustrated and in its operation may be made by those skilled in the art without departing from the spirit of the invention. It is the invention, therefore, to be limited only as indicated by the scope of the claims appended hereto.

What is claimed is:

1. A system for reducing the acoustic levels of internal and external sound fields generated by gas turbine engines of a jet aircraft having an aircraft fuselage, wings, nacelles, tail, and stabilizer structures, said system comprising
   a plurality of actuator means to generate sound,
   a plurality of sensor means to measure said acoustic levels, said sensor means comprising microphone means located in and around the engines, and on a plurality of aircraft structures selected from among the aircraft fuselage, wings, nacelles, tail, and stabilizer structures,
   one or more controller means to control said actuators to generate sound in order to effect the reduction of the internal and external sound field as measured by the plurality of sensors
   wherein said actuator means comprises an air modulator-based acoustic source that receives a flow of compressed air derived from compression stages of one or more of said engines.

2. A system for reducing the acoustic levels of internal and external sound fields generated by gas turbine engines of a jet aircraft having an aircraft fuselage, wings, nacelles, tail, and stabilizer structures, said system comprising
   a plurality of actuator means to generate sound,
   a plurality of sensor means to measure said acoustic levels, said sensor means comprising microphone means located in and around the engines, and on a plurality of aircraft structures selected from among the aircraft fuselage, wings, nacelles, tail, and stabilizer structures,
   one or more controller means to control said actuators to generate sound in order to effect the reduction of the internal and external sound field as measured by the plurality of sensors
   wherein said engines have external far and near acoustic radiation fields and said sensor means comprise
   first error sensors located inside the engine, and
   second error sensors located in the far and near external acoustic radiation fields of the engine.

3. A system for reducing the acoustic levels of internal and external sound fields generated by gas turbine engines of a jet aircraft having an aircraft fuselage, wings, nacelles, tail, and stabilizer structures, said system comprising
   a plurality of actuator means to generate sound,
   a plurality of sensor means to measure said acoustic levels, said sensor means comprising microphone means located in and around the engines, and on a plurality of aircraft structures selected from among the aircraft fuselage, wings, nacelles, tail, and stabilizer structures,
   one or more controller means to control said actuators to generate sound in order to effect the reduction of the internal and external sound field as measured by the plurality of sensors
   wherein
   said controller means receives signals from a plurality of said sensors and comprises
   means to control a plurality of actuator means simultaneously to suppress acoustic noise from multiple engines.

4. A system for reducing the acoustic levels of internal and external sound fields generated by gas turbine engines of a jet aircraft having an aircraft fuselage, wings, nacelles, tail, and stabilizer structures, said system comprising
   a plurality of actuator means to generate sound,
   a plurality of sensor means to measure said acoustic levels, said sensor means comprising microphone means located in and around the engines, and on a plurality of aircraft structures selected from among the aircraft fuselage, wings, nacelles, tail, and stabilizer structures,
   one or more controller means to control said actuators to generate sound in order to effect the reduction of the internal and external sound field as measured by the plurality of sensors
   wherein said engines provide signals to keyphasor or tachometer means and said controller receives rotational cycle reference signals from the keyphasor or tachometer means,
   wherein said engines provide a rotational cycle reference signal and said sensor means provide signals to said controller and said system further comprises
   means to convert signals from the sensors to digital samples, said means to convert operating at a sampling rate, and
   rotational speed synchronization means to synchronize the sampling rate to the engines rotational cycle reference signal.

5. A jet aircraft having an active system for reducing the acoustic levels of internal and external sound fields generated by gas turbine engines of the jet aircraft comprising
   a plurality of actuator means to generate sound,
   a plurality of sensor means to measure said acoustic levels, said sensor means comprising
   one or more controller means for controlling said actuators to radiate acoustic energy to cancel acoustic levels measured by said sensor means,
   said jet engine having a nacelle comprising
   a cowl,
   an inlet duct,
   engine and cowl panels,
   a bypass duct,
   an exhaust duct that comprises
   a tailpipe extension,
   thrust reverser, and
   tailpipe,
   said nacelle having zones containing noise source sensors, internal error sensors, external error sensors, and canceling actuators,
   said aircraft having forward and rearward ends, wherein said nacelle has an inlet end and comprises
   a nose cowl having an inlet duct at the inlet end of said nacelle, an engine and cowl panel having a bypass duct immediately behind said nose cowl, a tail pipe extension behind said engine and cowl panel, said tailpipe extension having an exhaust duct and a thrust reverser and tail pipe behind said tail pipe extension, wherein said zones comprising noise source sensors comprise a first noise source sensor zone in the forward end of said engine and cowl panel, a second noise source sensor zone in the forward end of said tail pipe extension and wherein said zones comprising error sensors comprise a first error sensor zone in the forward end of said nose cowl, a second error sensor zone in the rearward end of said engine and cowl panel, and a third error sensor zone in said thrust reverser and tail pipe, actuator zones comprising a first actuator zone in the inlet duct of said nose cowl aft of said first error sensor zone, a second actuator zone in the bypass duct of said engine and cowl panel between said first noise source sensor zone and said second error sensor zone, and a third actuator zone located in the exhaust duct of said tailpipe extension located aft of said second noise source sensor zone.

6. The jet aircraft of claim 5 wherein the actuators located in one or more of said first, second and third actuator zones comprise air stream modulators.

7. The jet aircraft of claim 5 wherein the actuators located in one or more of said first, second and third actuator zones comprise piezoceramic actuators.

8. The jet aircraft of claim 6 wherein one or more of said air stream modulators comprises an air modulator actuator horn having a mouth opening into an ambient bypass air flow, said horn comprising throat means to provide impedance loading to enhance performance, and horn section means to match the impedance of the ambient bypass air flow at the mouth of the horn.

9. The jet aircraft of claim 8 wherein said horn comprises a mouth having a flange attached to an entry hole in an engine bypass duct wall, a plenum, and a pipe manifold attached to a source of air.

10. The jet aircraft of claim 9 wherein said engine comprises compressor stages and bleed ports on the engine's compressor stages, and wherein said pipe manifold is adapted to receive compressed air from said bleed ports.

11. The jet aircraft of claim 10 wherein said throat means of said horn provides an exit from the plenum, and said mouth of said horn provides an entrance back into a bypass duct, each engine having a plurality of air modulator actuators.

12. The jet aircraft of claim 11 wherein said horn comprises driver means.

13. The jet aircraft of claim 12 wherein said driver means comprises a stiffness-controlled, electrodynamic actuator.

14. A jet aircraft having an active system for reducing the acoustic levels of internal and external sound fields generated by gas turbine engines of the jet aircraft comprising plurality of actuator means to generate sound, a plurality of sensor means to measure said acoustic levels, said sensor means comprising one or more controller means for controlling said actuators to radiate acoustic energy to cancel acoustic levels measured by said sensor means, said jet engine having a nacelle comprising a cowl, an inlet duct, engine and cowl panels, a bypass duct.

an exhaust duct that comprises a tailpipe extension, thrust reverser, and tailpipe, said nacelle having zones containing noise source sensors, internal error sensors, external error sensors, and canceling actuators wherein said actuator means comprise acoustic loudspeakers located in one or more of the inlet duct, a bypass duct and the forward end of the tailpipe.

* * * * *